(12) United States Patent
Palepu

(10) Patent No.: US 8,541,465 B2
(45) Date of Patent: *Sep. 24, 2013

(54) DOCETAXEL FORMULATIONS WITH LIPOIC ACID AND/OR DIHYDROLIPOIC ACID

(75) Inventor: Nageswara R. Palepu, Southampton, PA (US)

(73) Assignee: SciDose, LLC, Amherst, MA (US)

( * ) Notice: Subject to any disclaimer, the term of this patent is extended or adjusted under 35 U.S.C. 154(b) by 567 days.

This patent is subject to a terminal disclaimer.

(21) Appl. No.: 12/589,145

(22) Filed: Oct. 19, 2009

(65) Prior Publication Data

US 2011/0092580 A1 Apr. 21, 2011

(51) Int. Cl.
*A61K 31/337* (2006.01)
*A61K 31/385* (2006.01)

(52) U.S. Cl.
USPC .......................................... 514/449; 514/440

(58) Field of Classification Search
None
See application file for complete search history.

(56) References Cited

U.S. PATENT DOCUMENTS

| | | | |
|---|---|---|---|
| 4,814,470 A | 3/1989 | Colin et al. | |
| 5,403,858 A | 4/1995 | Bastard et al. | |
| 5,438,072 A | 8/1995 | Bobee et al. | |
| 5,698,582 A | 12/1997 | Bastart et al. | |
| 5,714,512 A | 2/1998 | Bastart et al. | |
| 5,750,561 A | 5/1998 | Bastart et al. | |
| 5,968,972 A | 10/1999 | Brooder et al. | |
| 6,071,952 A | 6/2000 | Owens et al. | |
| 6,136,846 A | 10/2000 | Rubinfeld et al. | |
| 6,153,644 A | 11/2000 | Owens et al. | |
| 6,245,805 B1 | 6/2001 | Broder et al. | |
| 6,319,943 B1 | 11/2001 | Joshi et al. | |
| 6,395,770 B1 | 5/2002 | Broder et al. | |
| 6,458,373 B1 | 10/2002 | Lambert et al. | |
| 6,479,540 B1 | 11/2002 | Constantinides et al. | |
| 6,509,370 B1 | 1/2003 | Joshi-Hangal et al. | |
| 6,531,139 B1 | 3/2003 | Gao et al. | |
| 6,610,735 B2 | 8/2003 | Broder et al. | |
| 6,660,286 B1 | 12/2003 | Lambert et al. | |
| 6,667,048 B1 | 12/2003 | Lambert et al. | |
| 6,727,280 B2 | 4/2004 | Palepu et al. | |
| 6,730,698 B2 | 5/2004 | Broder et al. | |
| 6,818,615 B2 | 11/2004 | Broder et al. | |
| 6,964,946 B1 | 11/2005 | Gutierrez-Rocca et al. | |
| 6,979,456 B1 | 12/2005 | Parikh et al. | |
| 6,982,282 B2 | 1/2006 | Lambert et al. | |
| 7,030,155 B2 | 4/2006 | Lambert et al. | |
| 7,041,640 B2 | 5/2006 | Broder et al. | |
| 7,115,565 B2 | 10/2006 | Gao et al. | |
| 7,223,770 B2 | 5/2007 | Zhang et al. | |
| 7,772,274 B1 * | 8/2010 | Palepu ........................ | 514/449 |
| 2002/0049158 A1 | 4/2002 | Woo et al. | |
| 2002/0102280 A1 | 8/2002 | Anderson | |
| 2002/0156125 A1 | 10/2002 | Broder et al. | |
| 2003/0027858 A1 | 2/2003 | Lambert et al. | |
| 2003/0087954 A1 | 5/2003 | Palepu et al. | |
| 2003/0105156 A1 | 6/2003 | Palepu et al. | |
| 2003/0109575 A1 | 6/2003 | Lambert et al. | |
| 2003/0147959 A1 | 8/2003 | Lambert et al. | |
| 2003/0170279 A1 | 9/2003 | Lambert et al. | |
| 2004/0022820 A1 | 2/2004 | Anderson | |
| 2004/0053993 A1 | 3/2004 | Constantinides et al. | |
| 2004/0127551 A1 | 7/2004 | Zhang et al. | |
| 2004/0202712 A1 | 10/2004 | Lambert et al. | |
| 2005/0004002 A1 | 1/2005 | Desai et al. | |
| 2005/0119340 A1 | 6/2005 | Anderson et al. | |
| 2005/0137213 A1 | 6/2005 | Cai et al. | |
| 2005/0142189 A1 | 6/2005 | Lambert et al. | |
| 2005/0148534 A1 | 7/2005 | Castellino et al. | |
| 2005/0152979 A1 | 7/2005 | Besman et al. | |
| 2005/0187147 A1 | 8/2005 | Newman et al. | |
| 2005/0232952 A1 | 10/2005 | Lambert et al. | |
| 2005/0238634 A1 | 10/2005 | Broder et al. | |
| 2005/0267201 A1 | 12/2005 | Gutierrez-roca et al. | |
| 2005/0272806 A1 | 12/2005 | Falotico et al. | |
| 2006/0003002 A1 | 1/2006 | Fikstad et al. | |
| 2006/0003976 A1 | 1/2006 | Zhang et al. | |
| 2006/0024360 A1 | 2/2006 | Chen | |
| 2006/0172014 A1 | 8/2006 | Curd et al. | |
| 2006/0188566 A1 | 8/2006 | Liversidge et al. | |
| 2006/0189679 A1 | 8/2006 | Holton et al. | |
| 2006/0223760 A1 | 10/2006 | Li et al. | |
| 2006/0229359 A1 | 10/2006 | Zhang et al. | |
| 2006/0234909 A1 | 10/2006 | Newman et al. | |

(Continued)

FOREIGN PATENT DOCUMENTS

| | | |
|---|---|---|
| KR | 10-2010-0018741 | 2/2010 |
| WO | 00/78247 | 12/2000 |
| WO | 01/72299 | 10/2001 |
| WO | 01/72300 | 10/2001 |
| WO | 02/26208 | 4/2002 |
| WO | 02/092077 | 11/2002 |
| WO | 03/057208 | 7/2003 |
| WO | 03/074027 | 9/2003 |
| WO | 2005/020962 | 3/2005 |
| WO | 2005/039554 | 5/2005 |
| WO | 2005/097105 | 10/2005 |
| WO | 2006/133510 | 12/2006 |
| WO | 2007/020085 | 2/2007 |
| WO | 2008/026048 | 3/2008 |
| WO | 2008/042841 | 4/2008 |
| WO | 2009/090614 | 7/2009 |

OTHER PUBLICATIONS

Eriox Product Literature Nov. 2007.
Taxotere® Prescribing Information, Nov. 2008.

*Primary Examiner* — James D Anderson
(74) *Attorney, Agent, or Firm* — Frommer Lawrence & Haug LLP; Sandra Kuzmich; Russell A. Garman

(57) ABSTRACT

Formulations comprising docetaxel or a salt thereof in combination with α-lipoic acid and/or dihydrolipoic acid and/or salts thereof in narrow concentration ranges have improved stability as concentrate liquid formulations and permit longer times between dilution from higher concentrations through completion of infusions prepared therefrom allowing for lesser waste and more efficient use of personnel in infusion preparation.

20 Claims, No Drawings

(56) References Cited

U.S. PATENT DOCUMENTS

| | | |
|---|---|---|
| 2006/0263434 A1 | 11/2006 | Desai et al. |
| 2006/0292186 A1 | 12/2006 | Garrigue et al. |
| 2007/0060635 A1 | 3/2007 | Broder et al. |
| 2007/0082838 A1 | 4/2007 | De et al. |
| 2007/0116729 A1 | 5/2007 | Palepu |
| 2007/0117744 A1 | 5/2007 | Desai et al. |
| 2007/0128289 A1 | 6/2007 | Zhao |
| 2007/0128290 A1 | 6/2007 | Desai et al. |
| 2007/0129448 A1 | 6/2007 | Desai et al. |
| 2007/0141093 A1 | 6/2007 | Zhang et al. |
| 2007/0166388 A1 | 7/2007 | Desai et al. |
| 2007/0207173 A1 | 9/2007 | Chen |
| 2007/0207196 A1 | 9/2007 | Zhang |
| 2007/0208044 A1 | 9/2007 | Cai et al. |
| 2007/0244113 A1 | 10/2007 | Cai et al. |
| 2007/0244114 A1 | 10/2007 | Cai et al. |
| 2007/0249601 A1 | 10/2007 | Cai et al. |
| 2007/0281934 A1 | 12/2007 | Buggy et al. |
| 2008/0146651 A1 | 6/2008 | Jee et al. |
| 2008/0319048 A1 | 12/2008 | Palepu et al. |
| 2009/0215882 A1 | 8/2009 | Bouzada et al. |
| 2009/0215883 A1 | 8/2009 | Bouzada et al. |
| 2009/0227549 A1 | 9/2009 | Palepu et al. |
| 2009/0318543 A1 | 12/2009 | Vu et al. |
| 2010/0015195 A1 | 1/2010 | Jain et al. |

\* cited by examiner

DOCETAXEL FORMULATIONS WITH LIPOIC ACID AND/OR DIHYDROLIPOIC ACID

CROSS-REFERENCE TO RELATED APPLICATIONS

Not Applicable.

STATEMENT REGARDING FEDERALLY SPONSORED RESEARCH OR DEVELOPMENT

Not Applicable

FIELD OF THE INVENTION

The present invention relates to formulations of docetaxel, generally; a solution of docetaxel, in an initial concentrate strength, an intermediate concentrate strength, and an infusion strength, and diluent solutions for use in diluting the initial concentrate, or diluent solutions for diluting the intermediate concentrate to infusion strength, or diluent fluids for diluting a solid composition to the initial concentrate strength, the intermediate concentrate strength or the infusion strength. The invention further relates to the use of lipoic acid, dihydrolipoic acid, pharmaceutically acceptable salts of either and combinations thereof in particular concentration ranges.

BACKGROUND OF THE INVENTION

Docetaxel is an antineoplastic agent belonging to the taxoid family being marketed by Sanofi-Aventis under trade name TAXOTERE® (injection concentrate of docetaxel and polysorbate 80). It is prepared by semisynthesis beginning with a precursor extracted from the renewable needle biomass of yew plants. The chemical name for docetaxel is (2R,3S)—N-carboxy-3-phenylisoserine, N-tert-butyl ester, 13-ester with 5beta-20-epoxy-1,2α,4,7β,10β,13α-hexahydroxytax-11-en-9-one 4-acetate 2-benzoate, trihydrate. Docetaxel has the following structural formula:

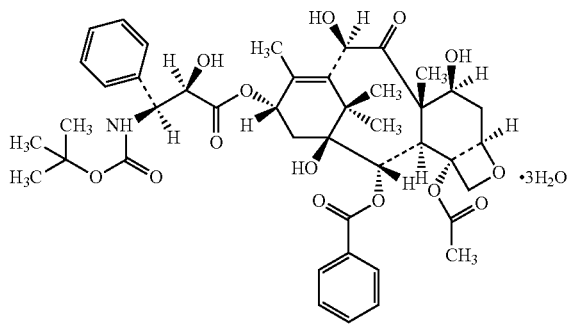

Docetaxel, as currently marketed by Sanofi-Aventis, is a white to almost-white powder with an empirical formula of $C_{43}H_{53}NO_{14} \cdot 3H_2O$, and a molecular weight of 861.9. It is highly lipophilic and practically insoluble in water. TAXOTERE® (docetaxel) Injection Concentrate is a clear yellow to brownish-yellow viscous solution. TAXOTERE® is sterile, non-pyrogenic, and is available in single-dose vials containing 20 mg (0.5 ml) or 80 mg (2 ml) docetaxel (on an anhydrous basis). Each ml contains 40 mg docetaxel (on an anhydrous basis) and 1040 mg polysorbate 80. For purposes of this specification, reference to an amount of "docetaxel" without reference to the specific form (i.e., hydrate, salt, etc.) will mean the stated amount of the free, anhydrous, non-solvated moiety of the drug in question unless the context clearly requires otherwise, notwithstanding the actual form of the compound then under discussion. Thus, for example, reference to 80.7 mg of docetaxel without reference to the form of the drug, means that amount of the actual drug form used which corresponds to the same number of moles of the docetaxel moiety as 80.7 mg of free, unsolvated, anhydrous docetaxel. If free docetaxel trihydrate were to be used, this would mean 86.1 mg of free docetaxel trihydrate. Similar calculations for salts and solvates will be apparent to those of ordinary skill in the art.

TAXOTERE® Injection Concentrate requires dilution prior to use. A sterile, non-pyrogenic, single-dose diluent is supplied for that purpose. The diluent for TAXOTERE® contains 13% ethanol in water for injection, and is supplied in vials. The preparation of the dilution is in two phases. The concentrate (which is stored between 2-25° C. (36 and 77° F.)) is allowed to come to room temperature, if not already, along with any necessary diluent (13% ethanol in water for injection for the commercially available material) by letting them stand under room temperature conditions for about 5 minutes. Diluent is aseptically withdrawn from its vial (approximately 1.8 ml for TAXOTERE®20 mg and approximately 7.1 ml for TAXOTERE® 80 mg) into a syringe by partially inverting the vial, and transferring it to the appropriate vial of TAXOTERE® Injection Concentrate. If the procedure is followed as described, an initial diluted solution of 10 mg docetaxel/ml will result. This initial dilution is mixed by repeated inversions for at least 45 seconds to assure full mixture of the concentrate and diluent. The vial should not be shaken. The resulting solution (10 mg docetaxel/ml) should be clear; however, there may be some foam on top of the solution due to the polysorbate 80. The initial diluted solution may be used immediately or stored either in the refrigerator or at room temperature for a maximum of 8 hours.

The current TAXOTERE® label indicates that the required amount of docetaxel is then aseptically withdrawn from the initial 10 mg docetaxel/ml solution with a calibrated syringe and injected into a 250 ml infusion bag or bottle of either 0.9% Sodium Chloride solution or 5% Dextrose solution to produce a final concentration of 0.3 to 0.74 mg/ml. If a dose greater than 200 mg of TAXOTERE® is required, a larger volume of the infusion vehicle is used so that a concentration of 0.74 mg/ml docetaxel is not exceeded. (It has been found that if this maximum is exceeded in the final infusion concentration, the TAXOTERE® precipitates out of the formulation having the polysorbate as the solubilizer.) The infusion is then thoroughly mixed by manual rotation. The final TAXOTERE® dilution for infusion should be administered intravenously as a 1-hour infusion under ambient room temperature and lighting conditions.

TAXOTERE® infusion solution, if stored between 2 and 25° C. (36 and 77° F.) is stable for 4 hours. Fully prepared TAXOTERE® infusion solution (in either 0.9% Sodium Chloride solution or 5% Dextrose solution) should be used within 4 hours (including the 1 hour intravenous administration).

The present marketed docetaxel (in TAXOTERE®) is dissolved in 100% (w/v) polysorbate 80 (Tween-80) which results in severe side effects. Severe hypersensitivity reactions characterized by generalized rash/erythema, hypotension and/or bronchospasm, or very rarely fatal anaphylaxis, have been reported in patients in spite of receiving the recommended 3-day dexamethasone premedication. Hypersensitivity reactions require immediate discontinuation of the TAXOTERE® infusion and administration of appropriate therapy. All the hypersensitive reactions mentioned above are primarily caused by and due to the presence of polysorbate 80 in the formulation. In order to reduce the side effects induced by polysorbate 80, all patients are treated with dexamethasone for three days prior to therapy. Dexamethasone is a steroid that suppresses the immune response in patients. Cancer patients under chemotherapy generally have a low level of immunity due to the destruction of healthy cells by the chemotherapeutic agents. Treatment with steroids will further compromise the patient's immunity and patients will be susceptible to bacterial and fungal attacks. Due to these side effects, most of the patients drop out of docetaxel therapy by the end of $2^{nd}$ or $3^{rd}$ cycle or skip a dose or continue further therapy at reduced dose. The recommended therapy is 6 cycles of docetaxel given once every three weeks. Thus, therapeutic activity and the maximum tolerated dose (MTD) of docetaxel are compromised due to the presence of polysorbate 80 in the formulation. Other solubilizing agents such as Cremophor EL (used in connection with the marketed paclitaxel product Taxol®) having similar allergic reactions (requiring pre-medication with steroids and antihistamines) should also be avoided.

The inventor's prior efforts at formulations of this type are seen in U.S. Ser. No. 12/214,506, filed Jun. 19, 2008, published as US 2008/0319048 on Dec. 25, 2008 and as WO/2009/002425 on Dec. 31, 2008. Those efforts included the use of a select number of solvents inclusive of glycofurol to prepare an initial concentrate, and a select number of diluent materials inclusive of TPGS, additional glycofurol, and optionally relatively large amounts of antioxidants for diluting the initial concentrate to an intermediate concentrate for use within a relatively short time to prepare the infusion for administration. Notwithstanding the advantages of those formulations, improvements thereover were still necessary and such improvements have resulted in the present invention.

OBJECTS OF THE INVENTION

It is therefore an object of one embodiment of the invention to provide a docetaxel formulation having an improved chemical stability, which upon dilution to an intermediate concentration so that the window for use after such dilution is greater than 8 hours, greater than 12 hours, greater than 16 hours, up to 24 hours.

It is an object of another embodiment of the invention to provide a docetaxel formulation suitable for injection or dilution to injection concentrations having greater than 8 hour, greater than 12 hours, greater than 16 hours, up to 24 hours stability containing a member selected from the group consisting of α-lipoic acid, dihydrolipoic acid, pharmaceutically acceptable salts of either and mixtures thereof.

It is an object of yet another embodiment of the invention to provide a docetaxel formulation containing a member selected from the group consisting of α-lipoic acid, dihydrolipoic acid, pharmaceutically acceptable salts of either and mixtures thereof in amounts of up to 2.5 parts by weight (based on free α-lipoic acid or dihydrolipoic acid respectively) per part relative to docetaxel (or pharmaceutically acceptable salt thereof based on free docetaxel) in such formulation.

Still another object of the invention is to provide a docetaxel/(α-lipoic acid or dihydrolipoic acid or pharmaceutically acceptable salts of either or mixtures thereof) formulation containing from greater than 0.025 parts to less than 2.5 parts of a member selected from the group consisting of α-lipoic acid, dihydrolipoic acid, pharmaceutically acceptable salts of either and mixtures thereof based on free α-lipoic acid or free dihydrolipoic acid, respectively) per part of docetaxel (or pharmaceutically acceptable salt thereof based on free docetaxel).

Still another object of the invention is to provide a diluent for a docetaxel concentrate which diluent contains α-lipoic acid or dihydrolipoic acid (or a pharmaceutically acceptable salt of either) in an amount sufficient that on dilution of (a) a docetaxel (or a pharmaceutically acceptable salt thereof) solid or liquid initial or intermediate concentrate results in (b) an intermediate concentration to fully diluted concentration of docetaxel (or a pharmaceutically acceptable salt thereof) suitable for injection where the α-lipoic acid or dihydrolipoic acid (or a pharmaceutically acceptable salt thereof) is in a fixed ratio to docetaxel (or a pharmaceutically acceptable salt thereof) in the range of more than 0.2 parts to less than 2.5 parts of a member selected from the group consisting of α-lipoic acid, dihydrolipoic acid, pharmaceutically acceptable salts of either and mixtures thereof per part of docetaxel (or a pharmaceutically acceptable salt thereof based on free docetaxel).

Another object of the invention is to provide a docetaxel liquid concentrate that further includes glycofurol and a member selected from the group consisting of α-lipoic acid, dihydrolipoic acid, pharmaceutically acceptable salts of either and mixtures thereof.

Still another object of the invention is to provide a docetaxel liquid concentrate that includes a member selected from the group consisting of α-lipoic acid, dihydrolipoic acid, pharmaceutically acceptable salts of either and mixtures thereof and is substantially free of polysorbate components and substantially free of Cremophor components.

An even further embodiment of the invention is to provide a docetaxel liquid concentrate that includes a member selected from the group consisting of α-lipoic acid, dihydrolipoic acid, pharmaceutically acceptable salts of either and mixtures thereof and is completely free of both polysorbate and Cremophor components.

It is yet another object of the invention to provide a docetaxel formulation that includes a member selected from the group consisting of α-lipoic acid, dihydrolipoic acid, pharmaceutically acceptable salts of either and mixtures thereof and has fewer hypersensitivity reactions than the currently commercially available formulations, which have a polysorbate 80 surfactant component.

It is yet another object of the invention to provide a docetaxel formulation that includes a member selected from the group consisting of α-lipoic acid, dihydrolipoic acid, pharmaceutically acceptable salts of either and mixtures thereof and has fewer hypersensitivity reactions than the currently commercially available formulations, which have a polysorbate surfactant component.

It is yet another object of the invention to provide a docetaxel formulation that includes a member selected from the group consisting of α-lipoic acid, dihydrolipoic acid, pharmaceutically acceptable salts of either and mixtures thereof and has fewer hypersensitivity reactions than the currently commercially available formulations, have a polysorbate 80 surfactant component and an alcohol component.

Still another object of the invention is to provide a substantially polysorbate-free docetaxel (or a pharmaceutically acceptable salt thereof) liquid concentrate formulation that includes a member selected from the group consisting of α-lipoic acid, dihydrolipoic acid, pharmaceutically acceptable salts of either and mixtures thereof and is also substantially free of hydroxyalkyl-substituted cellulosic polymers.

An even further object of the invention is to provide a substantially polysorbate-free and substantially Cremophor-free docetaxel (or a pharmaceutically acceptable salt thereof) liquid concentrate formulation that is free of hydroxyalkyl-substituted cellulosic polymers.

Still another object of the invention is to provide a substantially polysorbate-free docetaxel (or a pharmaceutically acceptable salt thereof) liquid concentrate formulation that includes a member selected from the group consisting of α-lipoic acid, dihydrolipoic acid, pharmaceutically acceptable salts of either and mixtures thereof and is also substantially free of substituted cellulosic polymers.

An even further object of the invention is to provide a substantially polysorbate-free and substantially Cremophor-free docetaxel (or a pharmaceutically acceptable salt thereof) liquid concentrate formulation that includes a member selected from the group consisting of α-lipoic acid, dihydrolipoic acid, pharmaceutically acceptable salts of either and mixtures thereof and is free of substituted cellulosic polymers.

Still another object of the invention is to provide a substantially polysorbate-free docetaxel (or a pharmaceutically acceptable salt thereof) liquid concentrate formulation that includes a member selected from the group consisting of α-lipoic acid, dihydrolipoic acid, pharmaceutically acceptable salts of either and mixtures thereof and is also substantially free of cellulosic polymers.

An even further object of the invention is to provide a substantially polysorbate-free and substantially Cremophor-free docetaxel (or a pharmaceutically acceptable salt thereof) liquid concentrate formulation that includes a member selected from the group consisting of α-lipoic acid, dihydrolipoic acid, pharmaceutically acceptable salts of either and mixtures thereof and is free of cellulosic polymers.

Still another object of the invention is to provide a suitable primary dilution formulation for use in preparing the aforementioned docetaxel (or a pharmaceutically acceptable salt thereof) liquid concentrates which primary dilution formulation contains a member selected from the group consisting of α-lipoic acid, dihydrolipoic acid, pharmaceutically acceptable salts of either and mixtures thereof.

An even further object of the invention is to provide a final dilution for injection of a docetaxel (or a pharmaceutically acceptable salt thereof) containing product that includes a member selected from the group consisting of α-lipoic acid, dihydrolipoic acid, pharmaceutically acceptable salts of either and mixtures thereof and is in the substantial absence or in the total absence of polysorbate 80 surfactant.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate 80 and in the substantial absence of Cremophor.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate 80 surfactant, in the substantial or total absence of Cremophor, and in the substantial or total absence of a hydroxyalkyl-substituted cellulosic polymer.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate 80 surfactant, in the substantial or total absence of Cremophor, in the substantial or total absence of a hydroxyalkyl-substituted cellulosic polymer, and in the substantial or total absence of alcohol.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate surfactant.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate and in the substantial absence of Cremophor.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate surfactant, in the substantial or total absence of Cremophor, and in the substantial or total absence of a hydroxyalkyl-substituted cellulosic polymer.

An even further object of the invention is to provide a final dilution for injection of a docetaxel (or a pharmaceutically acceptable salt thereof) containing product further containing a member selected from the group consisting of α-lipoic acid, dihydrolipoic acid, pharmaceutically acceptable salts of either and mixtures thereof in the substantial absence or in the total absence of polysorbate surfactant, in the substantial or total absence of Cremophor, in the substantial or total absence of a hydroxyalkyl-substituted cellulosic polymer, and in the substantial or total absence of alcohol.

Still another object of the invention is to provide a suitable primary dilution for use in preparing the aforementioned final dilution for injection formulations of docetaxel (or a pharmaceutically acceptable salt thereof).

An even further object of the invention is to provide a docetaxel (or a pharmaceutically acceptable salt thereof) lyophilizate for reconstitution where the lyophilizate further contains a member selected from the group consisting of α-lipoic acid, pharmaceutically acceptable salts of either and mixtures thereof in an amount of less than 2.5 parts by weight based on free α-lipoic acid per part of docetaxel (or a pharmaceutically acceptable salt thereof) by weight based on free docetaxel.

Yet another object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of polysorbate 80 surfactant and substantially free or totally free of a cremophor surfactant.

Yet another object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of polysorbate 80 surfactant, substantially free or totally free of a cremophor surfactant, and substantially free or totally free of a hydroxyalkyl-substituted cellulosic polymer.

Yet another object of the invention is to provide a docetaxel (or a pharmaceutically acceptable salt thereof) lyophilizate for reconstitution where the lyophilizate is substantially free or totally free of polysorbate 80 surfactant, substantially free or totally free of a cremophor surfactant, substantially free or totally free of a hydroxyalkyl-substituted cellulosic polymer, and substantially free of alcohol.

An even further object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of a polysorbate surfactant.

Yet another object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of a polysorbate surfactant and substantially free or totally free of a cremophor surfactant.

Yet another object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of a polysorbate surfactant, substantially free or totally free of a cremophor surfactant, and substantially free or totally free of a hydroxyalkyl-substituted cellulosic polymer.

Yet another object of the invention is to provide a docetaxel (or a pharmaceutically acceptable salt thereof) lyophilizate for reconstitution where the lyophilizate further contains a member selected from the group consisting of α-lipoic acid, dihydrolipoic acid, pharmaceutically acceptable salts of either and mixtures thereof and is substantially free or totally free of a polysorbate 80 surfactant, substantially free or totally free of a cremophor surfactant, substantially free or totally free of a hydroxyalkyl-substituted cellulosic polymer, and substantially free of alcohol.

Still another object of the invention is to provide a lyophilizate of docetaxel (or a pharmaceutically acceptable salt thereof) that can be reconstituted without the use of polysorbate 80 surfactant in either the lyophilizate or in the diluents for reconstitution and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Yet another object of the invention is to provide a lyophilizate of docetaxel (or a pharmaceutically acceptable salt thereof) that can be reconstituted without the use of polysorbate 80 surfactant and without the use of Cremophor surfactant in either the lyophilizate or in the reconstitution diluents and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Another object of the invention is to provide a lyophilizate of docetaxel (or a pharmaceutically acceptable salt thereof) that can be reconstituted without the use of any of polysorbate 80, Cremophor, and a hydroxyalkyl-substituted cellulosic polymer in either the lyophilizate or in the reconstitution diluents and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Still another object of the invention is to provide a lyophilizate of docetaxel (or a pharmaceutically acceptable salt thereof) that can be reconstituted without the use of any of polysorbate 80, Cremophor, a hydroxyalkyl-substituted cellulosic polymer and alcohol in either the lyophilizate or in the reconstitution diluents and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Still another object of the invention is to provide a lyophilizate of docetaxel (or a pharmaceutically acceptable salt thereof) that can be reconstituted without the use of a polysorbate surfactant in either the lyophilizate or in the diluents for reconstitution and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Yet another object of the invention is to provide a lyophilizate of docetaxel (or a pharmaceutically acceptable salt thereof) that can be reconstituted without the use of a polysorbate surfactant and without the use of a Cremophor surfactant in either the lyophilizate or in the diluents for reconstitution and wherein α-lipoic acid (or a pharmaceutically acceptable salt thereof) is present in at least one of the lyophilizate and the diluents formulation for reconstitution thereof.

Another object of the invention is to provide a lyophilizate of docetaxel (or a pharmaceutically acceptable salt thereof) that can be reconstituted without the use of any of a polysorbate surfactant, a Cremophor, and a substituted cellulosic polymer in either the lyophilizate or in the diluents for reconstitution and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Still another object of the invention is to provide a lyophilizate of docetaxel (or a pharmaceutically acceptable salt thereof) that can be reconstituted without the use of any of a polysorbate surfactant, a Cremophor, a substituted cellulosic polymer and alcohol in either the lyophilizate or in the diluents for reconstitution and wherein a member selected from the group consisting of α-lipoic acid, dihydrolipoic acid, pharmaceutically acceptable salts of either and mixtures thereof is present in at least one of the lyophilizate and the diluents formulation for reconstitution thereof.

Yet another object of the invention is to provide formulations, liquid concentrates, lyophilizates, etc. containing docetaxel (or a pharmaceutically acceptable salt thereof) that contain a member selected from the group consisting of α-lipoic acid, dihydrolipoic acid, pharmaceutically acceptable salts of either and mixtures thereof and are substantially free or totally free of any cellulosic polymer and can be reconstituted or diluted without the use a substantial amount or without the use of any amount of a cellulosic polymer.

Another object of the invention is to provide a means to administer docetaxel (or a pharmaceutically acceptable salt thereof) to patients without the need for administering dexamethasone or any other steroid and/or without the need to administer an antihistamine prior to the initiation of the docetaxel administration.

Yet another object of the invention is the avoidance of diarrheal side effect accompanying docetaxel administration primarily, if not totally, due to the polysorbate present in currently marketed docetaxel injection products.

An even further object of the invention is to provide a means to administer docetaxel (or a pharmaceutically acceptable salt thereof) to patients without the need for administering dexamethasone or any other steroid and/or without the need to administer an antihistamine prior to the initiation of the docetaxel administration and without the need for administering dexamethasone or any other steroid or antihistamine during or after the docetaxel (or a pharmaceutically acceptable salt thereof) administration for reasons related to hypersensitivity to the docetaxel or pharmaceutically acceptable salt thereof administration.

Still a further object of the invention is to provide formulations of docetaxel (or a pharmaceutically acceptable salt thereof) having an antioxidant amount of a member selected from the group consisting of α-lipoic acid, dihydrolipoic acid, thioaminoacids, propyl gallate, BHT, BHA and pharmaceutically acceptable salts of either and mixtures thereof which is present from about 500 parts by weight to 20,000 parts by weight per million parts by weight of docetaxel (or a pharmaceutically acceptable salt thereof based on free docetaxel) except in the case of lipoic acid or dihydrolipoic acid or their respective pharmaceutically acceptable salts which when present are present as discussed elsewhere in this specification.

Yet another object of the invention is to provide a diluent solution for a docetaxel (or a pharmaceutically acceptable salt thereof) solution in a solvent for docetaxel (or a pharmaceutically acceptable salt thereof), which diluent solution contains a member selected from the group consisting of α-lipoic acid, dihydrolipoic acid, pharmaceutically acceptable salts of either and mixtures thereof in an amount of from >0.025 parts to 2.0 parts by weight (based on free α-lipoic acid or dihydrolipoic acid respectively) relative to 1 part by weight docetaxel (or a pharmaceutically acceptable salt thereof based on free docetaxel).

Still another object of the invention is to provide a docetaxel (or a pharmaceutically acceptable salt thereof) formulation having a first amount of α-lipoic acid (or a pharmaceutically acceptable salt thereof) and a diluent solution therefor having a second amount of a member selected from the group consisting of α-lipoic acid, dihydrolipoic acid, pharmaceutically acceptable salts of either and mixtures thereof, such that on dilution of the docetaxel (or a pharmaceutically acceptable salt thereof) formulation with the diluent solution therefor, the resulting diluted formulation contains a member selected from the group consisting of α-lipoic acid, dihydrolipoic acid, pharmaceutically acceptable salts of either and mixtures thereof in the range of >0.025 parts by weight to 2.0 parts by weight (based on free α-lipoic acid or free dihydrolipoic acid respectively) relative to 1 part by weight of docetaxel (or a pharmaceutically acceptable salt thereof based on free docetaxel).

An even further object of the invention is to provide an infusion solution having a member selected from the group consisting of α-lipoic acid, dihydrolipoic acid, pharmaceutically acceptable salts of either and mixtures thereof present in an amount of >0.025 parts to 2.0 parts by weight (based on free α-lipoic acid or dihydrolipoic acid respectively) relative to 1 part by weight docetaxel (or a pharmaceutically acceptable salt thereof based on free docetaxel).

Yet another object of the invention is to provide a solid formulation of docetaxel (or a pharmaceutically acceptable salt thereof) having a member selected from the group consisting of α-lipoic acid, pharmaceutically acceptable salts of either and mixtures thereof present, the α-lipoic acid (or a pharmaceutically acceptable salt thereof) being present in an amount of not more than 1.5 parts by weight (based on free α-lipoic acid or relative to 1 part by weight docetaxel (or a pharmaceutically acceptable salt thereof based on free docetaxel).

Still a further object of the invention is to provide a solid formulation of docetaxel (or a pharmaceutically acceptable salt thereof) having a member selected from the group consisting of α-lipoic acid, pharmaceutically acceptable salts of either and mixtures thereof present in an amount of from >0.025 parts to 1.5 parts by weight (based on free α-lipoic acid or respectively) relative to 1 part by weight docetaxel (or a pharmaceutically acceptable salt thereof based on free docetaxel).

Still further objects of the invention will be appreciated by those of ordinary skill in the art.

BRIEF SUMMARY OF THE INVENTION

These and other objects of the invention can be achieved by a composition comprising docetaxel (or a pharmaceutically acceptable salt thereof) and (a) at least one pharmaceutically acceptable solubilizer excipient that can dissolve the docetaxel (or a pharmaceutically acceptable salt thereof) in amounts corresponding to at least 55 mg free docetaxel/ml or (b) a mixture of pharmaceutically acceptable hydrotropes that in concert (although not individually) are capable of dissolving docetaxel (or a pharmaceutically acceptable salt thereof) in amounts corresponding to at least 55 mg free docetaxel/ml or (c) mixtures thereof or (d) at least one pharmaceutically acceptable solubilization excipient that can dissolve docetaxel (or a pharmaceutically acceptable salt thereof) in amounts corresponding to at least 55 mg free docetaxel/ml in combination with at least one pharmaceutically acceptable solubilization aid where the solubilization aid does not alone or in combination with other solubilization aids dissolve docetaxel or a pharmaceutically acceptable slat thereof in amounts corresponding to at least 55 mg free docetaxel/ml and wherein at least one of the solid docetaxel, the initial concentrate thereof in a solubilizer or hydrotrope blend or solubilizer or one or more of the individual hydrotropes, or a diluent formulation for diluting any of the foregoing to either an intermediate concentration or to an infusion strength formulation contains a member selected from the group consisting of α-lipoic acid, dihydrolipoic acid, pharmaceutically acceptable salts of either and mixtures thereof in an mount such that by the time the docetaxel (or a pharmaceutically acceptable salt thereof) is at or below 10 mg (based on free docetaxel/ml) of solution strength, the a member selected from the group consisting of α-lipoic acid, dihydrolipoic acid, pharmaceutically acceptable salts of either and mixtures thereof is present with the docetaxel (or a pharmaceutically acceptable salt thereof) and in an amount of from greater than 0.025 parts up to 2.5 parts by weight based on free α-lipoic acid or dihydrolipoic acid respectively relative to 1 part by weight docetaxel (or a pharmaceutically acceptable salt thereof based on free docetaxel). It is surprisingly found that the lipoic acid and/or dihydrolipoic acid and/or pharmaceutically acceptable salts thereof in these ranges impart surprisingly valuable stability to the compositions of the invention. These docetaxel (or pharmaceutically acceptable salts thereof) solutions are either in the pharmaceutically acceptable solubilizer, hydrotropes, or mixtures thereof directly or in water solutions thereof, generally without further solubilization aids, but further such solubilization aids may be included if desired. Each of the solutions of the invention is preferably, but need not be, in the substantial absence of polysorbate 80, if not the total absence of polysorbate 80 and optionally in the substantial absence of or total absence of one or more of a polyethoxylated vegetable oil, a polyethoxylated castor oil, a polyethoxylated partially hydrogenated vegetable oil, a polyethoxylated partially hydrogenated castor oil, a polyethoxylated hydrogenated vegetable oil, a polyethoxylated hydrogenated castor oil, optionally in the substantial absence of or in the total absence of hydroxypropylmethylcellulose (preferably hydroxyalkyl alkylcellulose, more preferably substituted cellulosic polymers), and optionally in the substantial absence of ethanol. When ethanol is not substantially present, it may still be used in the preparation of a lyophilizate, but it is substantially, if not totally removed during the lyophilization process. The avoidance of the polysorbate 80 and Cremophor type solubilizers has the advantage that this avoids the hypersensitivity reactions that plague existing formulations of taxanes and allows for the reduction or elimination of steroid and/or antihistamine pre- and/or post treatment necessitated by concerns of hypersensitivity. Avoidance of the polysorbate 80 further avoids the diarrheal side effect caused thereby. Regardless of whether these materials are present or absent, the presence of the a member selected from the group consisting of α-lipoic acid, dihydrolipoic acid, pharmaceutically acceptable salts of either and mixtures thereof provides enhanced stability during long term storage and/or enhanced storage stability time once diluted to intermediate or final administration conditions. Thus the inclusion of the a member selected from the group consisting of α-lipoic acid, dihydrolipoic acid, pharmaceutically acceptable salts of either and mixtures thereof component allows for an extension of the suitable time frame in which one can utilize diluted docetaxel solution, thereby improving efficiency in the extemporaneous dilution of docetaxel formulations for injection and the elimination of substantial waste of materials. Where the polysorbates and polyethoxylated oils are avoided, the formulations allow for better, more effective dosing regimens and better patient compliance with recommended dosings than with the currently marketed taxane injectables.

BRIEF DESCRIPTION OF THE SEVERAL VIEWS OF THE DRAWING

Not Applicable

DETAILED DESCRIPTION OF THE INVENTION

The present invention is directed to (a) formulations of docetaxel, (b) concentrates for preparing injectable formulations of docetaxel, (c) docetaxel lyophilizates for reconstituting into such injectable compositions or into such concentrates for further dilution into such compositions; and further to (d) methods of manufacture of each. Methods of treatment of docetaxel treatable conditions with the docetaxel formulations, especially for treatment without the need for steroid pre-treatment or at least a reduction in the amount of steroid pre-treatment as compared to the present methods of administering docetaxel are also part of the invention as is the treatment without the need for antihistamine pre/post-treatment. The formulations, concentrates, lyophilizates, intermediate dilutions, and final administration injectable presentations are substantially free, preferably totally free of polysorbate 80, more preferably substantially free, still more preferably totally free of any polysorbate surfactant. Surprisingly stable products of the invention are prepared by the inclusion of lipoic acid or dihydrolipoic acid or pharmaceutically acceptable salts thereof in amounts (based on the non-salt forms thereof) that are in the range of more than 0.025 parts to less than 0.25 parts by weight relative to 1 part of docetaxel or pharmaceutically acceptable salt thereof (based on free docetaxel) that is present in the formulation or that upon dilution of a docetaxel formulation therewith, will have these components in the recited ranges.

If docetaxel is formulated with non-toxic pharmaceutically acceptable excipients, it can be administered to cancer patients at much higher doses (greater than the current dosing range of 75 to 100 mg/m$^2$), or higher infusion rates (up to at least 1 mg/ml in 10 to 15 minutes infusion time), for longer exposure to the drug (more than 6 cycles), and/or less than 3 weeks between cycles; and without missing any dosing cycles or dose reduction due to side effects. In other words, if docetaxel is formulated with pharmaceutically acceptable innocuous excipients, it will be better tolerated in cancer patients and would be highly beneficial to them as they can take the medication for a longer period of time without dose interruption and reduction (and therefore potentially higher total and cumulative dose) compared to the current formulation. Longer exposure to the docetaxel maintains the dose density over a longer period in the tumor and thereby helps to better eradicate the cancer cells and minimizes the relapse of the disease. Furthermore, the reduction or elimination of the steroid pre-treatment phase (in common use with the existing marketed docetaxel product) means fewer concerns with immune system depression, drug-drug interactions with other drugs which the patient may be taking, and the avoidance of side effects of steroid administration. Still further, avoidance of the Tween component (polysorbate component) means removal of a substantial cause of the diarrheal and erythema side effects seen with current docetaxel infusions. Finally, with the removal of the polysorbate component (and optional removal of the alcohol component) and enablement of administration at higher dosages than currently suitable, docetaxel (or a pharmaceutically acceptable salt thereof) may now be used to treat conditions which it could not previously be used to treat because of the dose limitations imposed by the polysorbate and/or alcohol components of the current TAXOTERE® formulation.

For purposes of the present invention, the terms "solubilizer" and "hydrotrope" will have the following definitions: A "solubilizer" is a solvent that is capable of dissolving docetaxel (or a pharmaceutically acceptable salt thereof) to prepare liquid concentrate in concentrations of at least greater than 55 mg docetaxel (or a pharmaceutically acceptable salt thereof based on free docetaxel) per ml of solution in the solvent or in an aqueous solution of the solvent, while a "hydrotrope" is defined as a material that is present in large quantities to solubilize the lipophilic drug (and further prevents the precipitation of docetaxel (or a pharmaceutically acceptable salt thereof) (or other lipophilic agent in the formulation) when the liquid concentrate is further diluted to lower concentrations)). A hydrotrope solubilizes docetaxel or any such other lipophilic agent and requires large quantities to dissolve the drug, but still does not dissolve the drug to the extent as the solubilizer, but two or more hydrotropes can act synergistically on solubility such that the combination can be used as a "solubilizer" in the context of the present invention (again provided that the docetaxel (or a pharmaceutically acceptable salt thereof) has a solubility in that synergistic combination of at least 55 mg (based on free docetaxel)/ml). In some instances a solubilizer can provide sufficient degree of dissolution that a separate hydrotrope or other solubilization aid is not needed, but this is generally not the case (i.e. a separate hydrotrope is usually desirable). For clarity, if a solvent can be used to yield a solution in the solvent directly or in a water solution thereof of docetaxel (or a pharmaceutically acceptable salt thereof) at least 55 mg/ml, preferably at least 60 mg/ml or more (each based on free docetaxel), it is a "solubilizer" according to the present invention. For example, Tween 80, glycofurol, ethanol, etc. can be classified as solubilizers while ethanol, TPGS 1000, PEG 400 and propylene glycol are classified as hydrotropes. The concentration of drug in solubilizer varies depending on the lipophilicity of drug. The table below shows a number of solubility studies with docetaxel. Each of the solvents that are reported to be able to dissolve docetaxel (or a pharmaceutically acceptable salt thereof) to an amount of at least about 55 mg/ml, preferably at least about 60 mg/ml each based on free docetaxel, is a "solubilizer" according to the present invention. Those of ordinary skill in the art will know of other suitable materials by either reference to literature or by conducting simple solubility studies such as those indicated in the Examples below. Some of the remaining materials where docetaxel solubility is greater than or equal to 10 mg/ml in the Table below can be seen to be "hydrotropes" according to the definitions of the present invention, with other materials being neither solubilizers nor hydrotropes but having some ability to dissolve docetaxel being "solubilization aids". The present invention generally, and preferably, does not use the polysorbates (Tweens) even though they are excellent solubilizers because of their tolerability problems as injectable solution components, and thus, the present invention is an attempt to obtain similar or better results (than the TAXOTERE® formulation) without the use of polysorbate surfactants. However, the use of α-lipoic acid (or a pharmaceutically acceptable salt thereof), even in the Tween containing formulations such as the currently marketed TAXOTERE® offers benefits and are within the scope of a lesser preferred embodiment of the invention. Some of the tested solvents, such as N-Methyl 2-Pyrrolidone Labrofac, peceol and maisine 35-1 are not used in the parenteral therapy, and are not materials for use in the invention. Solubility studies conducted with these excipients are to understand how different excipients containing different functional groups are contributing to the solubility of docetaxel. A solubilizer can also act as a hydrotrope (on dilution with infusion fluid) if it is used in the sufficiently large quantities. For example, docetaxel (or a pharmaceutically acceptable salt thereof) solubility (based on free docetaxel) in glycofurol is about 200 mg/ml. When this liquid concentrate is diluted with water to administration concentrations, docetaxel precipitates out. Hence a special diluent is needed to dilute the liquid concentrate to prevent precipitation of docetaxel. If docetaxel is prepared as about a 10 mg/ml solution in glycofurol, it will not precipitate out when diluted with IV fluids to administration concentrations. Thus, by decreasing drug (based on free docetaxel) to glycofurol ratio from 200:1 w/w to about 10:1 w/w (20-fold increase in glycofurol level), glycofurol functions as a solubilizer (in the concentrate) as well as a hydrotrope (in the diluted infusion solution concentration. In the table below and the rest of this specification, the terms "solubilizer" and "hydrotrope" will be used with reference to concentrates (both initial and intermediate) unless specifically indicated otherwise or the context so requires.

| | | |
|---|---|---|
| PEG 400 | 10 mg/ml | Hydrotrope |
| Propylene Glycol | 10 mg/ml | Hydrotrope |
| 50% PEG 400/50% PG | 15 mg/ml | Hydrotrope |
| 2% Lutrol in PEG 400 | 15 mg/ml | Hydrotrope |
| Tween 80 | 60 mg/ml | Solubilizer |
| Tween 20 | 90 mg/ml | Solubilizer |
| Glycerol | 1.65 mg/ml | Solubilization aid |
| Span 80 | 3.5 mg/ml | Solubilization aid |
| TPGS 1000 | 50 mg/ml | Hydrotrope |
| Labrofac (Capric triglyceride PEG 4 ester•Macrogol 200) | 35 mg/ml | Hydrotrope |
| Peceol (Glycerol mono Oleate 40) | 7 mg/ml | Solubilization aid |
| Maisine 35-1 (Glycerol mono linoleate) | 10 mg ml | Hydrotrope |
| Ethanol | 120 mg/ml | Solubilizer |
| N-Methyl 2-Pyrrolidone | 17.6 mg/ml | Hydrotrope |
| Benzyl alcohol | 90 mg/ml | Solubilizer |
| Benzyl benzoate | 13 mg/ml | Hydrotrope |
| Acetic acid | 60 mg/ml | Solubilizer |
| l-lactic acid | 6 mg/ml | Solubilization aid |
| Glycofurol | 200 mg/ml | Solubilizer |
| Dihydrolipoic acid | >120 mg/ml | Solubilizer |

Even though some of the tested solvents showed very high solubility of docetaxel therein and would allow the manufacture of liquid concentrates, in a number of instances, on dilution with water and other common diluents (for the preparation of injectable products, such as normal saline or 5% dextrose solution), the docetaxel came out of solution. Thus, the mere suitability of a solvent as a solubilizer is not enough to complete the present invention. Behavior upon dilution with suitable injectable diluent solutions (water for injection, saline solutions, or dextrose solution for injection) needs to be explored as well in order to obtain a suitable product. Such further exploration will be within the ability of one of ordinary skill in the art once aware of the present disclosures.

Notwithstanding the above, the solubilizers for the present invention can be selected (without limitation) from the group consisting of glycofurol, acetic acid, N-β-hydroxyethyl lactamide, benzyl alcohol and ethanol. Ethanol, which may be present in certain embodiments, is preferably absent, more preferably totally absent. In the embodiments in which it is present, it may be present in an amount that upon dilution of the doxetaxel (or pharmaceutically acceptable salt thereof) containing portion to 10 mg (based on free docetaxel)/ml solution, the ethanol should not exceed 13% w/v of such solution. In most embodiments, ethanol is not present in any significant amount (typically less than about 2000 ppm, preferably less than about 1000 ppm, more preferably less than about 500 ppm, still more preferably less than about 250 ppm, and most preferably not more than about 200 ppm), and in many embodiments is completely absent. Other solvents (those not acceptable for being present in the final formulation for injection) for docetaxel may be used in the preparation of the docetaxel (or pharmaceutically acceptable salt thereof) in the form to be used (such as in a crystallization or lyophilization process provided they are removed before utilization of the docetaxel in the preparation of the solutions for use in the present invention, but preferably they are not employed even in these preparative procedures.

Glycofurol is also known as tetrahydrofurfuryl alcohol polyethylene glycol ether and has the following structure:

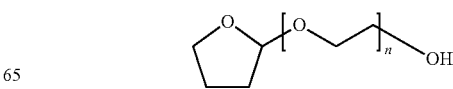

where n is on average 2 for glycofurol 75, but may be other integers for other glycofurols. Glycofurol, especially glycofurol 75, is one of the most preferred solubilizers as docetaxel is highly soluble therein (200 mg/ml in glycofurol 75). While glycofurol 75 is the most preferred of the glycofurols, those having an average n in the above formula of about 2 to about 8, preferably 2 to about 6, more preferably 2 to about 4, more preferably about 2 or about 3 or about 4 are also suitable. Larger values of n can be used, but the appropriateness of the larger glycofurols (average n in excess of about 8) falls off quickly.

Hydrotropes for the present invention are generally selected (without limitation) from the group consisting of polyethylene glycol, especially PEG 400; propylene glycol, Lutrol 2% in PEG (especially in PEG 400); tocopherol compounds, particularly tocopherol-polyethylene glycols, more particularly tocopherol polyethylene glycol diacid (such as succinates, maleates, etc.) esters, especially tocopherol polyethyleneglycol succinates, most preferably tocopherol polyethylene glycol 1000 succinate (TPGS 1000); Labrofac; Peceol; Maisine 35-I; N-methyl-2-pyrrolidone; benzyl benzoate; ethyl carbonate, propylene carbonate, propylene glycol; 1,3-butylene glycol; $C_{1-4}$alkylesters of $C_{12-18}$saturated, mono unsaturated or di-unsaturated fatty acids, especially ethyl oleate; dioxolanes; glycerol formal; dimethylisosorbide, solketal; gentisic acid; and mixtures thereof. Labrofac; Peceol; Maisine 35-I; and N-methyl-2-pyrrolidone are generally not suitable for injectable use and therefore, these materials are least desired to be used, and should be generally avoided. Some mixtures of the hydrotropes will act synergisitically on the solubility of docetaxel such that the combination can be used as the "solubilizer" of the present invention. Confirmation of which combinations of hydrotropes that will act synergistically on solubility so as to be so used as a solubilizer can be done in routine solubility experiments which are totally within the ordinary skill within the art. When such combinations are used in place of a material which is a solubilizer in its own right, the formulation may contain (a) additional amounts of one of the hydrotropes of the synergistic combination or (b) a different hydrotrope or (c) neither, or may further contain a solubilization aid if so desired.

Docetaxel (or pharmaceutically acceptable salt thereof) active agent can be dissolved in the solubilizer (solubilizer includes mixtures of hydrotropes that have the requisite solubility of docetaxel therein to qualify the mixture as a solubilizer) alone or in a mixture of the solubilizer and hydrotrope to obtain a clear solution (i.e. initial high concentrate formulation). This can be in the presence or absence of water and preferably is in the absence of water. When the hydrotrope is to be present in the initial high concentrate solution, it is preferably added to the solubilizer first and the docetaxel (either alone or in solution with a solubilizer) is added to the solubilizer/hydrotrope solution, although other orders of addition are suitable as well. These can then be lyophilized and the lyophilizate reconstituted to form concentrates using solvents, hydrotropes, solubilization aids selected from the previously set forth group of materials other than those that are specifically indicated as being avoided and other than those that are not compatible with injectable formulations. The initial high concentrate solution can be stored at room temperature or under refrigeration conditions, preferably refrigerated conditions (preferably about 2 to about 8° C.). The concentrate solution is then diluted with a first diluent that contains solubilizer and optionally hydrotrope (whether or not hydrotrope is present in the initial concentrate already) or may be diluted with just injectable diluent fluid alone if the solubilizer/hydrotrope are both already present, or with diluent having one or both of the solubilizer and/or hydrotrope regardless of whether the solubilizer/hydrotrope are otherwise present to obtain an intermediate concentrated solution generally in the concentration range of 5-20 mg docetaxel/ml or higher, preferably about 10 mg/ml (although other intermediate concentrations can be formed as well). This intermediate concentrate is further diluted with an injectable diluent solution (generally water for injection, normal saline solution, or dextrose 5% for injection) to concentrations of 0.3 to 0.74 mg (based on free docetaxel)/ml, for administration designed to be in the same concentration range as that recommended in the currently marketed TAXOTERE® product; however, as discussed earlier, higher infusion concentrations (at least up to 1 mg docetaxel (or pharmaceutically acceptable salt thereof based on free docetaxel)/ml or higher) as well as faster infusion rates are also suitable for the present invention since there is no polysorbate component present. If the hydrotrope is not present in the concentrate formulation, then the diluent solution to prepare the intermediate concentrate should either have the appropriate amount of hydrotrope present or the hydrotrope may be added separately to the concentrate at a point in time before dilution with the injectable diluent solution. If desired, the initial high concentrate solution may be diluted directly by the injectable diluent (normal saline, water for injection, or D5W for example) to achieve the TAXOTERE® recommended administrable concentration of not more than about 0.74 mg docetaxel per ml (or higher if desired) if the initial high concentration solution has sufficient amounts of both the solubilizer and hydrotrope present, although it is best to prepare the dilution in the two step process set out above. In a highly preferred embodiment, the docetaxel (or pharmaceutically acceptable salt thereof) is dissolved in a solubilizer (preferably glycofurol) to a concentration of about 40 mg/ml or about 80 mg/ml (each based on free docetaxel) or higher with or without an antioxidant (preferably selected from α-lipoic acid, dihydrolipoic acid, and pharmaceutically acceptable salts thereof) to form a first (or initial) concentrate solution. Separately, a primary diluent formulation is prepared comprising at least one hydrotrope (preferably TPGS 1000 and/or PEG 400), optionally additional solubilizer (preferably selected from glycofurol and/or ethanol), with water and optionally suitable amounts of a tonicity adjuster and optionally suitable amounts of a buffer or other pH modifier. Where TPGS is one of the hydrotropes, it is present in the primary diluent preferably at a concentration of about 100 mg/ml to about 290 mg/ml (750 mg, 1000 mg, 1250 mg, 1500 mg, 1750 mg, and 2000 mg per 7 ml of primary diluents being preferred). When PEG 400 is one of the hydrotropes used, it is preferably present in present in amounts of 2.0-3.5 ml per 7 ml of primary diluents.

The member selected from the group consisting of α-lipoic acid, dihydrolipoic acid, pharmaceutically acceptable salts of either and mixtures thereof component is present in the present invention in an amount (based on free α-lipoic acid or free dihydrolipoic acid respectively) in proportion to the docetaxel (or pharmaceutically acceptable salt thereof based on free docetaxel) when in the intermediate concentration formulation strength of up to 2.5 parts, preferably not more than 2.0 parts, more preferably not more than 1.0 parts, still more preferably not more than 0.75 parts, even more preferably not more than 0.5 parts, still even more preferably not more than 0.25 parts (based on free α-lipoic acid or free dihydrolipoic acid respectively) per part of docetaxel (or pharmaceutically acceptable salt thereof based on free docetaxel); preferably from about 0.025 parts to about 0.2 parts, more preferably about 0.03125 parts to about 0.1875 parts, still more preferably about 0.0375 parts to about 0.1275 parts, even more preferably from about 0.05 parts to about 0.09375 parts, most preferably about 0.0625 parts (based on free α-lipoic acid or dihydrolipoic acid respectively) per part of docetaxel (or pharmaceutically acceptable salt thereof based on free docetaxel). Prior to formation of the intermediate concentration formulation, the α-lipoic acid, dihydrolipoic acid, pharmaceutically acceptable salts of either and mixtures thereof component can be incorporated in whole or in part into the solid docetaxel (or pharmaceutically acceptable salt thereof), the initial concentrate, or the diluent formulation for dilution of the solid material or the diluent formulation for dilution of the initial concentration formulation into the intermediate concentration formulation, or any combination thereof so that once diluted to the intermediate concentration formulation the requisite total amounts of a member selected from the group consisting of α-lipoic acid, dihydrolipoic acid, pharmaceutically acceptable salts of either and mixtures thereof is present as set forth above.

Preferred formulations for the diluent for diluting an 80 mg docetaxel (or pharmaceutically acceptable salt thereof based on free docetaxel)/ml initial concentrate into a 10 mg docetaxel (or pharmaceutically acceptable salt thereof based on free docetaxel)/ml intermediate concentrate contain (a) TPGS 1000, (b) PEG 400, (c) optionally a member selected from the group consisting of α-lipoic acid, dihydrolipoic acid, pharmaceutically acceptable salts of either and mixtures thereof, preferably α-lipoic acid or a pharmaceutically acceptable salt thereof preferably present if the initial concentration docetaxel formulation to be diluted has insufficient amounts of this component to meet the requirements set forth for this component elsewhere), (d) water if needed to bring the primary diluent formulation volume to 7 ml, (e) optionally sodium or potassium chloride, and (f) optionally ethanol. 7 ml of this primary diluent is used to dilute every 1 ml of the 80 mg/ml solution described above to result in a 10 mg docetaxel (or pharmaceutically acceptable salt thereof)/ml intermediate concentrate formulation which is then ready to be added in an appropriate amount to an infusion solution for infusion administration in appropriate therapeutic infusion strengths. More preferably, sample diluent formulations are, without limitation set forth in the table below, but formulations B and BG are most highly preferred when all of the α-lipoic acid (or pharmaceutically acceptable salt thereof) is contained in the primary diluent formulation. Corresponding primary diluent formulations are also deemed set forth having lesser amounts of the α-lipoic acid or salt thereof when a portion of the α-lipoic acid, dihydrolipoic acid or salts thereof are contained in the initial concentrate, and corresponding primary diluent formulations having no α-lipoic acid or salt thereof are also contemplated for diluting initial concentrates where the initial concentrate already has the full requirement of the α-lipoic acid, dihydrolipoic acid or salts thereof. For these corresponding formulations, those corresponding to formulations B and BG below are, without limitation also preferred.

All amounts in the following table are in mg unless noted otherwise:

|    | TPGS 1000 | PEG 400 (in ml) | α-lipoic acid | α-lipoic acid potassium salt (based on free α-lipoic acid) | NaCl | Ethanol (in ml) | Water (q.s. to stated ml) |
|----|-----------|-----------------|---------------|-----------------------------------------------------------|------|-----------------|---------------------------|
| A  | 750       | 3.5             | 5.0           |                                                           | 72   | 0.9             | 7.0                       |
| B  | 1000      | 3.5             | 5.0           |                                                           | 72   | 0.9             | 7.0                       |
| C  | 1250      | 3.5             | 5.0           |                                                           | 72   | 0.9             | 7.0                       |
| D  | 1500      | 3.5             | 5.0           |                                                           | 72   | 0.9             | 7.0                       |
| E  | 1750      | 3.5             | 5.0           |                                                           | 72   | 0.9             | 7.0                       |
| F  | 750       | 3.5             | 2.5           |                                                           | 72   | 0.9             | 7.0                       |
| G  | 1000      | 3.5             | 2.5           |                                                           | 72   | 0.9             | 7.0                       |
| H  | 1250      | 3.5             | 2.5           |                                                           | 72   | 0.9             | 7.0                       |
| I  | 1500      | 3.5             | 2.5           |                                                           | 72   | 0.9             | 7.0                       |
| J  | 1750      | 3.5             | 2.5           |                                                           | 72   | 0.9             | 7.0                       |
| K  | 750       | 3.5             | 3.0           |                                                           | 72   | 0.9             | 7.0                       |
| L  | 1000      | 3.5             | 3.0           |                                                           | 72   | 0.9             | 7.0                       |
| M  | 1250      | 3.5             | 3.0           |                                                           | 72   | 0.9             | 7.0                       |
| N  | 1500      | 3.5             | 3.0           |                                                           | 72   | 0.9             | 7.0                       |
| O  | 1750      | 3.5             | 3.0           |                                                           | 72   | 0.9             | 7.0                       |
| P  | 750       | 3.5             | 4.0           |                                                           | 72   | 0.9             | 7.0                       |
| Q  | 1000      | 3.5             | 4.0           |                                                           | 72   | 0.9             | 7.0                       |
| R  | 1250      | 3.5             | 4.0           |                                                           | 72   | 0.9             | 7.0                       |
| S  | 1500      | 3.5             | 4.0           |                                                           | 72   | 0.9             | 7.0                       |
| T  | 1750      | 3.5             | 4.0           |                                                           | 72   | 0.9             | 7.0                       |
| U  | 750       | 3.5             | 4.5           |                                                           | 72   | 0.9             | 7.0                       |
| V  | 1000      | 3.5             | 4.5           |                                                           | 72   | 0.9             | 7.0                       |
| W  | 1250      | 3.5             | 4.5           |                                                           | 72   | 0.9             | 7.0                       |
| X  | 1500      | 3.5             | 4.5           |                                                           | 72   | 0.9             | 7.0                       |
| Y  | 1750      | 3.5             | 4.5           |                                                           | 72   | 0.9             | 7.0                       |
| Z  | 750       | 3.5             | 5.5           |                                                           | 72   | 0.9             | 7.0                       |
| AA | 1000      | 3.5             | 5.5           |                                                           | 72   | 0.9             | 7.0                       |
| AB | 1250      | 3.5             | 5.5           |                                                           | 72   | 0.9             | 7.0                       |
| AC | 1500      | 3.5             | 5.5           |                                                           | 72   | 0.9             | 7.0                       |
| AD | 1750      | 3.5             | 5.5           |                                                           | 72   | 0.9             | 7.0                       |
| AE | 750       | 3.5             | 6.0           |                                                           | 72   | 0.9             | 7.0                       |
| AF | 1000      | 3.5             | 6.0           |                                                           | 72   | 0.9             | 7.0                       |
| AG | 1250      | 3.5             | 6.0           |                                                           | 72   | 0.9             | 7.0                       |
| AH | 1500      | 3.5             | 6.0           |                                                           | 72   | 0.9             | 7.0                       |
| AI | 1750      | 3.5             | 6.0           |                                                           | 72   | 0.9             | 7.0                       |
| AJ | 750       | 3.5             | 10            |                                                           | 72   | 0.9             | 7.0                       |
| AK | 1000      | 3.5             | 10            |                                                           | 72   | 0.9             | 7.0                       |
| AL | 1250      | 3.5             | 10            |                                                           | 72   | 0.9             | 7.0                       |

-continued

| | TPGS 1000 | PEG 400 (in ml) | α-lipoic acid | α-lipoic acid potassium salt (based on free α-lipoic acid) | NaCl | Ethanol (in ml) | Water (q.s. to stated ml) |
|---|---|---|---|---|---|---|---|
| AM | 1500 | 3.5 | 10 | | 72 | 0.9 | 7.0 |
| AN | 1750 | 3.5 | 10 | | 72 | 0.9 | 7.0 |
| AO | 750 | 3.5 | 15 | | 72 | 0.9 | 7.0 |
| AP | 1000 | 3.5 | 15 | | 72 | 0.9 | 7.0 |
| AQ | 1250 | 3.5 | 15 | | 72 | 0.9 | 7.0 |
| AR | 1500 | 3.5 | 15 | | 72 | 0.9 | 7.0 |
| AS | 1750 | 3.5 | 15 | | 72 | 0.9 | 7.0 |
| AT | 750 | 3.5 | 20 | | 72 | 0.9 | 7.0 |
| AU | 1000 | 3.5 | 20 | | 72 | 0.9 | 7.0 |
| AV | 1250 | 3.5 | 20 | | 72 | 0.9 | 7.0 |
| AW | 1500 | 3.5 | 20 | | 72 | 0.9 | 7.0 |
| AX | 1750 | 3.5 | 20 | | 72 | 0.9 | 7.0 |
| AY | 750 | 3.5 | 22.5 | | 72 | 0.9 | 7.0 |
| AZ | 1000 | 3.5 | 22.5 | | 72 | 0.9 | 7.0 |
| BA | 1250 | 3.5 | 22.5 | | 72 | 0.9 | 7.0 |
| BB | 1500 | 3.5 | 22.5 | | 72 | 0.9 | 7.0 |
| BC | 1750 | 3.5 | 22.5 | | 72 | 0.9 | 7.0 |
| BD | 750 | 3.5 | 5.0 | | 72 | | 7.0 |
| BE | 1000 | 3.5 | 5.0 | | 72 | | 7.0 |
| BF | 1250 | 3.5 | 5.0 | | 72 | | 7.0 |
| BG | 1500 | 3.5 | 5.0 | | 72 | | 7.0 |
| BH | 1750 | 3.5 | 5.0 | | 72 | | 7.0 |
| BI | 750 | 3.5 | 2.5 | | 72 | | 7.0 |
| BJ | 1000 | 3.5 | 2.5 | | 72 | | 7.0 |
| BK | 1250 | 3.5 | 2.5 | | 72 | | 7.0 |
| BL | 1500 | 3.5 | 2.5 | | 72 | | 7.0 |
| BM | 1750 | 3.5 | 2.5 | | 72 | | 7.0 |
| BN | 750 | 3.5 | 3.0 | | 72 | | 7.0 |
| BO | 1000 | 3.5 | 3.0 | | 72 | | 7.0 |
| BP | 1250 | 3.5 | 3.0 | | 72 | | 7.0 |
| BQ | 1500 | 3.5 | 3.0 | | 72 | | 7.0 |
| BR | 1750 | 3.5 | 3.0 | | 72 | | 7.0 |
| BS | 750 | 3.5 | 4.0 | | 72 | | 7.0 |
| BT | 1000 | 3.5 | 4.0 | | 72 | | 7.0 |
| BU | 1250 | 3.5 | 4.0 | | 72 | | 7.0 |
| BV | 1500 | 3.5 | 4.0 | | 72 | | 7.0 |
| BW | 1750 | 3.5 | 4.0 | | 72 | | 7.0 |
| BX | 750 | 3.5 | 4.5 | | 72 | | 7.0 |
| BY | 1000 | 3.5 | 4.5 | | 72 | | 7.0 |
| BZ | 1250 | 3.5 | 4.5 | | 72 | | 7.0 |
| CA | 1500 | 3.5 | 4.5 | | 72 | | 7.0 |
| CB | 1750 | 3.5 | 4.5 | | 72 | | 7.0 |
| CC | 750 | 3.5 | 5.5 | | 72 | | 7.0 |
| CD | 1000 | 3.5 | 5.5 | | 72 | | 7.0 |
| CE | 1250 | 3.5 | 5.5 | | 72 | | 7.0 |
| CF | 1500 | 3.5 | 5.5 | | 72 | | 7.0 |
| CG | 1750 | 3.5 | 5.5 | | 72 | | 7.0 |
| CH | 750 | 3.5 | 6.0 | | 72 | | 7.0 |
| CI | 1000 | 3.5 | 6.0 | | 72 | | 7.0 |
| CJ | 1250 | 3.5 | 6.0 | | 72 | | 7.0 |
| CK | 1500 | 3.5 | 6.0 | | 72 | | 7.0 |
| CL | 1750 | 3.5 | 6.0 | | 72 | | 7.0 |
| CM | 750 | 3.5 | 10 | | 72 | | 7.0 |
| CN | 1000 | 3.5 | 10 | | 72 | | 7.0 |
| CO | 1250 | 3.5 | 10 | | 72 | | 7.0 |
| CP | 1500 | 3.5 | 10 | | 72 | | 7.0 |
| CQ | 1750 | 3.5 | 10 | | 72 | | 7.0 |
| CR | 750 | 3.5 | 15 | | 72 | | 7.0 |
| CS | 1000 | 3.5 | 15 | | 72 | | 7.0 |
| CT | 1250 | 3.5 | 15 | | 72 | | 7.0 |
| CU | 1500 | 3.5 | 15 | | 72 | | 7.0 |
| CV | 1750 | 3.5 | 15 | | 72 | | 7.0 |
| CW | 750 | 3.5 | 20 | | 72 | | 7.0 |
| CX | 1000 | 3.5 | 20 | | 72 | | 7.0 |
| CY | 1250 | 3.5 | 20 | | 72 | | 7.0 |
| CZ | 1500 | 3.5 | 20 | | 72 | | 7.0 |
| DA | 1750 | 3.5 | 20 | | 72 | | 7.0 |
| DB | 750 | 3.5 | 22.5 | | 72 | | 7.0 |
| DC | 1000 | 3.5 | 22.5 | | 72 | | 7.0 |
| DE | 1250 | 3.5 | 22.5 | | 72 | | 7.0 |
| DF | 1500 | 3.5 | 22.5 | | 72 | | 7.0 |
| DG | 1750 | 3.5 | 22.5 | | 72 | | 7.0 |
| DH | 1000 | 3.5 | 5.0 | | | 0.9 | 7.0 |
| DI | 1000 | 3.5 | 5.0 | | 36 | 0.9 | 7.0 |
| DJ | 1500 | 3.5 | 5.0 | | | | 7.0 |

-continued

|  | TPGS 1000 | PEG 400 (in ml) | α-lipoic acid | α-lipoic acid potassium salt (basedon free α-lipoic acid) | NaCl | Ethanol (in ml) | Water (q.s. to stated ml) |
|---|---|---|---|---|---|---|---|
| DK | 1500 | 3.5 | 5.0 |  | 36 |  | 7.0 |
| DL | 1000 | 3.0 | 5.0 |  |  | 0.9 | 7.0 |
| DM | 1000 | 3.0 | 5.0 |  | 36 | 0.9 | 7.0 |
| DN | 1000 | 3.0 | 5.0 |  | 72 | 0.9 | 7.0 |
| DO | 1500 | 2.5 | 5.0 |  |  |  | 7.0 |
| DP | 1500 | 2.5 | 5.0 |  | 36 |  | 7.0 |
| DQ | 1500 | 2.5 | 5.0 |  | 72 |  | 7.0 |
| DR | 1000 | 3.0 |  | 5.0 |  | 0.9 | 7.0 |
| DS | 1000 | 3.0 |  | 5.0 | 36 | 0.9 | 7.0 |
| DT | 1000 | 3.0 |  | 5.0 | 72 | 0.9 | 7.0 |
| DU | 1500 | 2.5 |  | 5.0 |  |  | 7.0 |
| DV | 1500 | 2.5 |  | 5.0 | 36 |  | 7.0 |
| DW | 1500 | 2.5 |  | 5.0 | 72 |  | 7.0 |
| DX | 1000 | 3.0 | 2.5 | 2.5 |  | 0.9 | 7.0 |
| DY | 1000 | 3.0 | 2.5 | 2.5 | 36 | 0.9 | 7.0 |
| DZ | 1000 | 3.0 | 2.5 | 2.5 | 72 | 0.9 | 7.0 |
| EA | 1500 | 2.5 | 2.5 | 2.5 |  |  | 7.0 |
| EB | 1500 | 2.5 | 2.5 | 2.5 | 36 |  | 7.0 |
| EC | 1500 | 2.5 | 2.5 | 2.5 | 72 |  | 7.0 |

Also preferred are the corresponding formulations wherein the α-lipoic acid is replaced by the same number of mg of dihydrolipoic acid or the α-lipoic acid potassium salt is replaced by the same number of mg of α-lipoic acid non-potassium pharmaceutically acceptable alkaline salt forms, or the same number of mg of dihydrolipoic acid or its pharmaceutically acceptable alkaline salt forms.

This liquid concentrate and the diluent solution may then be packaged and stored for commercial distribution. The diluent solution is then used to dilute the docetaxel concentrate to an intermediate concentration of about 5 to about 20 mg docetaxel/ml, preferably about 8 to about 15 mg docetaxel/ml, more preferably about 10 mg docetaxel/ml. The intermediate concentration solution is then diluted to administration concentrations with normal saline, 5% dextrose, or other suitable injection diluents for administration to the patient. In all preferred cases, polysorbate 80 is limited to very minor amounts (substantially free of polysorbate 80), or is completely absent, preferably completely absent; more preferably any polysorbate is substantially absent and most preferably completely absent from the foregoing. In some embodiments, the lyophilizates, liquid concentrates, the intermediate concentrates, and the diluted for administration formulations are substantially free of, more preferably totally free of Cremophor, and preferably substantially free of, still more preferably totally free of all polyethoxylated vegetable oils (whether totally hydrogenated, partially hydrogenated, or not hydrogenated). In other embodiments, the lyophilizates, liquid concentrates, the intermediate concentrates, and the diluted for administration formulations are substantially free of, still more preferably totally free of ethanol. In yet further embodiments, the lyophilizates, liquid concentrates, the intermediate concentrates, and the diluted for administration formulations are substantially free of, preferably totally free of hydroxyalkyl substituted cellulosic polymers (preferably substituted cellulosic polymers, more preferably cellulosic polymers). Still other embodiments are substantially free, if not totally free of each of the aforementioned polysorbates, polyethoxylated vegetable oils (whether hydrogenated in whole or in part or not hydrogenated), and substituted cellulosic polymers, and in some preferred embodiments ethanol.

In addition to merely dissolving the docetaxel, the docetaxel "as is" or in the presence of TPGS 1000 and/or the α-lipoic acid or salts thereof can be lyophilized and presented as a lyophilizate for reconstitution to a concentrate material (of either the initial high concentrate formulation concentrations or directly to the intermediate concentrate formulations or even directly to the administrable concentrations depending on whether the lyophilizate contains the member selected from the group consisting of α-lipoic acid, dihydrolipoic acid, pharmaceutically acceptable salts of either and mixtures thereof in the requisite amounts). The lyophilization procedure can be a routine lyophilization using an appropriate solvent for lyophilization purposes. Insofar as the lyophilization solvent is driven off in the course of the lyophilization procedure, lyophilization may use solvents that are not suitable for parenteral administration, but generally will use suitable materials for parenteral use. The docetaxel solution for lyophilization need not be a solution using a solubilizer or a hydrotrope of the present invention as the solubilizer and hydrotrope may then be added after the lyophile is formed, at any of before, at, or upon reconstitution. However, if desired and the particular solubilizer and/or hydrotrope and/or solubilization aids and/or a member selected from the group consisting of α-lipoic acid, dihydrolipoic acid, pharmaceutically acceptable salts of either and mixtures thereof that remain in the lyophilizate during and through the lyophilization procedure, they may be added to the docetaxel solution before lyophilization so that the lyophilizate contains the appropriate amounts of docetaxel and optionally one or more solubilizers and/or hydrotropes and optionally one or more solubilization aids and optionally the member selected from the group consisting of α-lipoic acid, dihydrolipoic acid, pharmaceutically acceptable salts of either and mixtures thereof of the present invention. In such situations as the lyophilizate contains both solubilizers and hydrotrope and/or the α-lipoic acid (or pharmaceutically acceptable salt thereof) in appropriate amounts, reconstitution with the appropriate amount of injectable diluent solution provides the complete formulation of some embodiments of the present invention. In each case, the lyophilizate, the concentrates made therefrom, the intermediate concentrates made therefrom, and the formulation in the administration concentration are each subject to the independent or concurrent restrictions set forth above with respect to polysorbates, Cremophors, polyethoxylated vegetable oils, hydroxyalkyl substituted cellulosic polymers, substituted cellulosic polymers, cellulosic polymers, and ethanol as stated more fully concerning the formulations made without the use of lyophilization.

In addition, as a means to offset the acidic nature of some of the components, a buffer can be added such as phosphate buffer (or other suitable buffer, such as without limitation, carbonate/bicarbonate buffer), generally in an amount of about 0.5 to about 2 mg of phosphate buffer for about each mg of a member selected from the group consisting of α-lipoic acid, dihydrolipoic acid, pharmaceutically acceptable salts of either and mixtures thereof or other acidic oxidative protectant in the formulation. The buffer may also be included in the pre-lyophilization solution, but is preferably added in the reconstitution or dilution steps. The buffer is selected so as to be capable to buffer the intermediate concentrate as well as the final infusion solution to a pH of about 5 to about 7.5, preferably about 5.5 to about 7.2, more preferably about 6 to about 7, most preferably about 6.5 to about 7. Appropriate amounts of the free acid or base used and its conjugate salt to create the buffer will be within the ability of those of ordinary skill in the art. Alternate organic buffer materials include, without limitation, the following materials together with their conjugate salts (which free compound/salt conjugate may form in situ from either the free compound or the conjugate salt being added alone as known in the art of buffer materials) adipic acid, amino acids such as, without limitation, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, etc. Potassium hydroxide or sodium hydroxide, preferably potassium hydroxide, can be used to make final pH adjustments upward. The amount of potassium hydroxide or sodium hydroxide used to bring pH in the region of 5 to 7.5 is preferably 25 to 40 mg, but more or less can be used as appropriate. Hydrochloric acid or additional phosphoric acid can be used as needed to make final pH adjustments downward. Bicarbonate or carbonate salts, especially sodium or potassium salts thereof, most preferably potassium salts thereof, may be used to adjust pH as well.

The initial concentration can be stored for long periods of time of up to about 2 years (730 days), preferably from about one year (365 days) to about one and half years (500) days, at room temperature and longer still under refrigeration. The intermediate concentrates can be stored at ambient temperatures for periods substantially in excess of 8 hours such as at least up to 12, at least up to 16, and at least up to 24 hours, and still greater periods when stored under refrigeration conditions; however, it is preferably utilized (including dilution to infusion strength and infusion administration time within 48 hours after preparation of the intermediate concentrate, more preferably within 36 hours, still more preferably within 30 hours, yet more preferably with 24 hours. Such preferred utilization times of the intermediate concentrate include within 23, 22, 21, 20, 19, 18, 17, 16, 15, 14, 13, 12, 11, 10, 9, 8, 7, 6, 5, 4, or fewer hours. The longer periods allow for preparation of intermediate concentrates for use once per day and potentially less frequently allowing for substantial savings in pharmacy preparation time, especially over weekends and holidays, when staff may be at reduced levels, whereas those that must be used within 8 hours or less (as in the case of TAXOTERE®) hospital pharmacies may need to prepare intermediate concentrates multiple times a day depending upon their usage needs. Once the intermediate concentrate is further diluted to the infusion concentration, the invention solutions can be used up to 8 (eight) hours or longer including the actual infusion administration time, but are preferably used in 5 hours or less. This allows for more efficient preparation and administration systems in hospitals and other care facilities, especially as compared to TAXOTERE® which requires use of the infusion, including the infusion administration time of no more than 4 hours.

As the present invention is directed to delivery of docetaxel, once diluted to appropriate injection (especially infusion, most particularly IV infusion) concentrations, it may be administered in appropriate amounts for treating docetaxel responsive conditions known in the art. In addition, since the present invention permits higher doses and concentrations than the currently marketed TAXOTERE®, the concentrates and administrable dosage forms thereof made from the present invention are also useful for many of the indications known in the art for docetaxel based on non-clinical data for which the current marketed TAXOTERE® formulation is not recommended because of an inability to administer docetaxel at a sufficiently high dose, either acutely or cumulatively. These include, without limitation, carcinomas such as colorectal, prostate, pancreatic and liquid tumors like lymphoma and leukemia.

The following examples are presented to exemplify, not limit, the scope of the present invention, which is only limited by the claims appended hereto.

Initial Concentrates Containing α-Lipoic Acid or a Salt Thereof

Examples 1-12

Example 1

α-lipoic acid is dissolved in glycofurol (glycofurol 75) in an amount of 5 mg/ml and free docetaxel active agent is dissolved therein to result in a final docetaxel moiety concentration of 80 mg/ml of solution.

Example 2

Example 1 is repeated except that the α-lipoic acid is added after the docetaxel, rather than before it.

Examples 3 and 4

Examples 1 and 2 are repeated except that α-lipoic acid potassium salt or sodium salt is used in place of the free α-lipoic acid in an amount equivalent to the same number of moles/ml as the free α-lipoic acid.

Examples 5-8

Examples 1-4 are repeated except that docetaxel hydrochloride is used in place of free docetaxel in an amount corresponding to the same number of moles/ml of 80 mg/ml of free docetaxel.

Examples 9-12

Examples 1-4 are repeated except that docetaxel trihydrate is used in place of free docetaxel in an amount corresponding to the same number of moles as 80 mg/ml of the free docetaxel.

Initial Concentrates Using Dihydrolipoic Acid or a Salt Thereof

Examples 13-24

Examples 13-24

Examples 1-12 are repeated except that 5 mg/ml dihydrolipoic acid or an amount equivalent to the same number of moles as 5 mg/ml of the free dihydrolipoic acid of the potassium or sodium salt thereof is used in place of the 5 mg/ml α-lipoic acid or potassium salt thereof of Examples 1-12.

Diluents for Initial Concentrates

Example 25

The following formulation is prepared for use to dilute the initial concentrates in Examples 1-24 above to intermediate concentrate concentrations of 10 mg docetaxel moiety/ml of intermediate concentrate.
1.5 gm TPGS
2.5 ml PEG-400
72 mg NaCl
Qs water to 7 ml.

Example 26

Example 25 is repeated except that the amount of TPGS, PEG, and NaCl are adjusted in accordance with the following table.

|    | TPGS | PEG-400 | Osmotic Agent | Optional additional |
|----|------|---------|---------------|---------------------|
| A  | 1.0 gm | 2.5 ml | 72 mg NaCl | — |
| B  | 1.25 gm | 2.5 ml | 72 mg NaCl | — |
| C  | 1.75 gm | 2.5 ml | 72 mg NaCl | — |
| D  | 2.0 gm | 2.5 ml | 72 mg NaCl | — |
| E  | 1.0 gm | 2.5 ml | 72 mg KCl | — |
| F  | 1.25 gm | 2.5 ml | 72 mg KCl | — |
| G  | 1.5 gm | 2.5 ml | 72 mg KCl | — |
| H  | 1.75 gm | 2.5 ml | 72 mg KCl | — |
| I  | 2.0 gm | 2.5 ml | 72 mg KCl | — |
| J  | 1.0 gm | 2.0 ml | 72 mg NaCl | — |
| K  | 1.25 gm | 2.0 ml | 72 mg NaCl | — |
| L  | 1.5 gm | 2.0 ml | 72 mg NaCl | — |
| M  | 1.75 gm | 2.0 ml | 72 mg NaCl | — |
| N  | 2.0 gm | 2.0 ml | 72 mg NaCl | — |
| O  | 1.0 gm | 3.0 ml | 72 mg NaCl | — |
| P  | 1.25 gm | 3.0 ml | 72 mg NaCl | — |
| Q  | 1.5 gm | 3.0 ml | 72 mg NaCl | — |
| R  | 1.75 gm | 3.0 ml | 72 mg NaCl | — |
| S  | 2.0 gm | 3.0 ml | 72 mg NaCl | — |
| T  | 1.0 gm | 2.0 ml | 72 mg KCl | — |
| U  | 1.25 gm | 2.0 ml | 72 mg KCl | — |
| V  | 1.5 gm | 2.0 ml | 72 mg KCl | — |
| W  | 1.75 gm | 2.0 ml | 72 mg KCl | — |
| X  | 2.0 gm | 2.0 ml | 72 mg KCl | — |
| Y  | 1.0 gm | 3.0 ml | 72 mg KCl | — |
| Z  | 1.25 gm | 3.0 ml | 72 mg KCl | — |
| AA | 1.5 gm | 3.0 ml | 72 mg KCl | — |
| AB | 1.75 gm | 3.0 ml | 72 mg KCl | — |
| AC | 2.0 gm | 3.0 ml | 72 mg KCl | — |
| AD | 1.0 gm | 2.5 ml | 36 mg NaCl | — |
| AE | 1.25 gm | 2.5 ml | 36 mg NaCl | — |
| AF | 1.5 gm | 2.5 ml | 36 mg NaCl | — |
| AG | 1.75 gm | 2.5 ml | 36 mg NaCl | — |
| AH | 2.0 gm | 2.5 ml | 36 mg NaCl | — |
| AI | 1.0 gm | 2.5 ml | 90 mg NaCl | — |
| AJ | 1.25 gm | 2.5 ml | 90 mg NaCl | — |
| AK | 1.5 gm | 2.5 ml | 90 mg NaCl | — |
| AL | 1.75 gm | 2.5 ml | 90 mg NaCl | — |
| AM | 2.0 gm | 2.5 ml | 90 mg NaCl | — |
| AN | 1.0 gm | 2.5 ml | — | — |
| AO | 1.25 gm | 2.5 ml | — | — |
| AP | 1.5 gm | 2.5 ml | — | — |
| AQ | 1.75 gm | 2.5 ml | — | — |
| AR | 2.0 gm | 2.5 ml | — | — |
| AS | 1.0 gm | 2.5 ml | 36 mg KCl | — |
| AT | 1.25 gm | 2.5 ml | 36 mg KCl | — |
| AU | 1.5 gm | 2.5 ml | 36 mg KCl | — |
| AV | 1.75 gm | 2.5 ml | 36 mg KCl | — |
| AW | 2.0 gm | 2.5 ml | 36 mg KCl | — |
| AX | 1.0 gm | 2.5 ml | 36 mg KCl | — |
| AY | 1.25 gm | 2.5 ml | 36 mg KCl | — |
| AZ | 1.5 gm | 2.5 ml | 36 mg KCl | — |
| BA | 1.75 gm | 2.5 ml | 36 mg KCl | — |
| BB | 2.0 gm | 2.5 ml | 36 mg KCl | — |
| BC | 1.0 gm | 2.5 ml | 72 mg NaCl | 0.9 ml ethanol |
| BD | 1.0 gm | 2.5 ml | 72 mg KCl | 0.9 ml ethanol |
| BE | 1.0 gm | 2.5 ml | 72 mg NaCl | 0.9 ml ethanol |
| BF | 1.0 gm | 2.5 ml | 72 mg NaCl | 0.9 ml ethanol |
| BG | 1.0 gm | 2.5 ml | 72 mg KCl | 0.9 ml ethanol |
| BH | 1.0 gm | 2.5 ml | 72 mg KCl | 0.9 ml ethanol |
| BI | 1.0 gm | 2.5 ml | 36 mg NaCl | 0.9 ml ethanol |
| BJ | 1.0 gm | 2.5 ml | 90 mg NaCl | 0.9 ml ethanol |
| BK | 1.0 gm | 2.5 ml | 90 mg NaCl | 0.9 ml ethanol |
| BL | 1.0 gm | 2.5 ml | — | 0.9 ml ethanol |
| BM | 1.0 gm | 2.5 ml | 36 mg KCl | 0.9 ml ethanol |
| BN | 1.0 gm | 2.5 ml | 36 mg KCl | 0.9 ml ethanol |
| BO | 1.25 gm | 2.5 ml | 72 mg NaCl | 0.9 ml ethanol |
| BP | 1.25 gm | 2.5 ml | 72 mg KCl | 0.9 ml ethanol |
| BQ | 1.25 gm | 2.5 ml | 72 mg NaCl | 0.9 ml ethanol |
| BR | 1.25 gm | 2.5 ml | 72 mg NaCl | 0.9 ml ethanol |
| BS | 1.25 gm | 2.5 ml | 72 mg KCl | 0.9 ml ethanol |
| BT | 1.25 gm | 2.5 ml | 72 mg KCl | 0.9 ml ethanol |
| BU | 1.25 gm | 2.5 ml | 36 mg NaCl | 0.9 ml ethanol |
| BV | 1.25 gm | 2.5 ml | 90 mg NaCl | 0.9 ml ethanol |
| BW | 1.25 gm | 2.5 ml | 90 mg NaCl | 0.9 ml ethanol |
| BX | 1.25 gm | 2.5 ml | — | 0.9 ml ethanol |
| BY | 1.25 gm | 2.5 ml | 36 mg KCl | 0.9 ml ethanol |
| BZ | 1.25 gm | 2.5 ml | 36 mg KCl | 0.9 ml ethanol |
| CA | 1.25 gm | 2.5 ml | 72 mg NaCl | 0.45 ml ethanol |
| CB | 1.25 gm | 2.5 ml | 72 mg KCl | 0.45 ml ethanol |
| CC | 1.25 gm | 2.0 ml | 72 mg NaCl | 0.45 ml ethanol |
| CD | 1.25 gm | 3.0 ml | 72 mg NaCl | 0.45 ml ethanol |
| CE | 1.25 gm | 2.0 ml | 72 mg KCl | 0.45 ml ethanol |
| CF | 1.25 gm | 3.0 ml | 72 mg KCl | 0.45 ml ethanol |
| CG | 1.25 gm | 2.5 ml | 36 mg NaCl | 0.45 ml ethanol |
| CH | 1.25 gm | 2.5 ml | 90 mg NaCl | 0.45 ml ethanol |
| CI | 1.25 gm | 2.5 ml | 90 mg NaCl | 0.45 ml ethanol |
| CJ | 1.25 gm | 2.5 ml | — | 0.45 ml ethanol |
| CK | 1.25 gm | 2.5 ml | 36 mg KCl | 0.45 ml ethanol |
| CL | 1.25 gm | 2.5 ml | 36 mg KCl | 0.45 ml ethanol |

Examples 27

The following formulation is prepared for use to dilute an initial concentrate of docetaxel that corresponds to the initial concentrates in Examples 1-24 except that the initial concentrates to be diluted with this example formulation are devoid of each α-lipoic acid, dihydrolipoic acid, and salts thereof.
5-25 mg α-lipoic acid
1.5 gm TPGS
2.5 ml PEG-400
72 mg NaCl
Qs water to 7 ml.

Example 28-32

Example 27 is repeated except that the 5-25 mg of α-lipoic acid is replaced by the same number of moles of one of α-lipoic acid sodium salt, α-lipoic acid potassium salt, dihydrolipoic acid, dihydrolipoic acid sodium salt, and dihydrolipoic acid potassium salt respectively.

Example 33

A concentrate of simply docetaxel 80 mg dissolved in glycofurol q.s to 1 ml is placed on stability testing under the conditions set forth in the Table below with the results set forth in the Table EX-33A. This formulation lacks the lipoic acid or dihydrolipoic acid or salts thereof component required in formulations of the present invention.

TABLE EX-33A

Stability of docetaxel liquid concentrate (80 mg/ml), lot# DCT-SOL-6

| Storage Temp. | Time period | Content mg/mL | % of Initial | RRT of Degradants | Degradant Area % | ID of Degradant |
|---|---|---|---|---|---|---|
| | Initial | 77.7 | 100 | 1.42 | 0.07 | Epi-DCT |
| 40° C. | 30 days | 76.6 | 99 | 0.21 | 0.11 | Unknown |
| | | | | 0.39 | 0.12 | Unknown |
| | | | | 0.48 | 0.05 | Unknown |
| | | | | 1.17 | 0.36 | 10-oxo-DCT |
| | | | | 1.43 | 0.12 | 7-Epi-DCT |
| | | | | Total | 0.76 | |
| | 60 days | 76.4 | 98 | 0.19 | 0.11 | Unknown |
| | | | | 0.29 | 0.05 | Unknown |
| | | | | 0.38 | 0.22 | Unknown |
| | | | | 0.46 | 0.09 | Unknown |
| | | | | 0.87 | 0.05 | Unknown |
| | | | | 1.18 | 0.45 | 10-oxo-DCT |
| | | | | 1.46 | 0.16 | 7-Epi-DCT |
| | | | | 1.64 | 0.09 | Unknown |
| | | | | Total | 1.22 | |
| | 90 days | 75.4 | 97 | 0.20 | 0.28 | Unknown |
| | | | | 0.35 | 0.12 | Unknown |
| | | | | 0.40 | 0.21 | Unknown |
| | | | | 0.46 | 0.05 | Unknown |
| | | | | 0.48 | 0.25 | Unknown |
| | | | | 0.52 | 0.05 | Unknown |
| | | | | 1.16 | 0.82 | 10-oxo-DCT |
| | | | | 1.44 | 0.26 | 7-Epi-DCT |
| | | | | 1.58 | 0.28 | 7-epi-10-oxo |
| | | | | Total | 2.32 | |
| 25° C. | 90 days | 76.9 | 99 | 0.88 | 0.05 | Unknown |
| | | | | 1.17 | 0.28 | 10-oxo-DCT |
| | | | | 1.45 | 0.09 | 7-Epi-DCT |
| | | | | Total | 0.42 | |
| | 180 days | 75.4 | 97 | 0.24 | 0.12 | Unknown |
| | | | | 0.40 | 0.18 | Unknown |
| | | | | 1.16 | 0.47 | 10-oxo-DCT |
| | | | | 1.44 | 0.27 | 7-Epi-DCT |
| | | | | 1.57 | 0.33 | 7-epi-10-oxo |
| | | | | Total | 1.37 | |
| | 360 days | 73.7 | 95 | 0.38 | 0.11 | Unknown |
| | | | | 0.46 | 0.12 | Unknown |
| | | | | 1.18 | 1.06 | 10-oxo-DCT |
| | | | | 1.47 | 0.41 | 7-Epi-DCT |
| | | | | 1.65 | 1.26 | Unknown |
| | | | | Total | 2.96 | |

We have also prepared the liquid concentrate in glycofurol at 40 mg/ml to mimic the innovator concentration. The stability data of this batch are summarized in Table EX-33B below. This formulation lacks the lipoic acid or dihydrolipoic acid or salts thereof component required in formulations of the present invention.

TABLE EX-33B

Stability of docetaxel liquid concentrate (40 mg/ml), lot# DCT-SOL-7

| Storage Temp. | Time period | Content mg/mL | % of Initial | RRT of Degradants | Degradant Area % | ID of Degradant |
|---|---|---|---|---|---|---|
| | Initial | 38.0 | 100 | 1.43 | 0.07 | Epi-DCT |
| 40° C. | 30 days | 37.6 | 99 | 0.21 | 0.12 | Unknown |
| | | | | 0.40 | 0.12 | Unknown |
| | | | | 0.48 | 0.05 | Unknown |
| | | | | 1.17 | 0.42 | 10-oxo-DCT |
| | | | | 1.43 | 0.13 | 7-Epi-DCT |
| | | | | Total | 0.84 | |
| | 60 days | 36.5 | 96 | 0.20 | 0.30 | Unknown |
| | | | | 0.31 | 0.09 | Unknown |
| | | | | 0.40 | 0.25 | Unknown |
| | | | | 0.48 | 0.11 | Unknown |

TABLE EX-33B-continued

Stability of docetaxel liquid concentrate (40 mg/ml), lot# DCT-SOL-7

| Storage Temp. | Time period | Content mg/mL | % of Initial | RRT of Degradants | Degradant Area % | ID of Degradant |
|---|---|---|---|---|---|---|
| | | | | 1.16 | 0.48 | 10-oxo-DCT |
| | | | | 1.44 | 0.15 | 7-Epi-DCT |
| | | | | 1.58 | 0.05 | 7-epi-10-oxo-dct |
| | | | | Total | 1.38 | |
| | 90 days | 35.4 | 93 | 0.20 | 0.36 | Unknown |
| | | | | 0.35 | 0.25 | Unknown |
| | | | | 0.40 | 0.19 | Unknown |
| | | | | 0.46 | 0.10 | Unknown |
| | | | | 0.48 | 0.34 | Unknown |
| | | | | 0.51 | 0.07 | Unknown |
| | | | | 1.16 | 1.00 | 10-oxo-DCT |
| | | | | 1.44 | 0.24 | 7-Epi-DCT |
| | | | | 1.58 | 0.26 | 7-epi-10-oxo-dct |
| | | | | Total | 2.81 | |
| 25° C. | 90 days | 37.5 | 99 | 0.20 | 0.07 | Unknown |
| | | | | 0.87 | 0.05 | Unknown |
| | | | | 1.16 | 0.24 | 10-oxo-DCT |
| | | | | 1.44 | 0.09 | 7-Epi-DCT |
| | | | | Total | 0.45 | |

TABLE EX-33C

Stability of docetaxel liquid concentrate, Marketed Product: Taxotere

| Lot ID | Storage Temp. | Time period | Content mg/mL | % of Initial | RRT of Degradants | Degradant Area % | ID of Degradant | Physical Observations |
|---|---|---|---|---|---|---|---|---|
| Mfg By: Sanofi-Aventis Lot#: | Initial | | 42.7 | 100.0 | 0.20 | 0.10 | Unknown | |
| | | | | | 0.35 | 0.05 | Unknown | |
| | | | | | 0.94 | 0.16 | Unknown | |
| | | | | | 1.18 | 0.11 | 10-oxo | |
| | | | | | 1.45 | 0.04 | 7-Epi-DCT | |
| D7A517 | | | | | Total | 0.46 | | |
| | 40° C. | 30 days | 42.5 | 99.0 | 0.20 | 0.13 | Unknown | |
| | | | | | 0.33 | 0.28 | Unknown | |
| | | | | | 0.37 | 0.11 | Unknown | |
| | | | | | 0.84 | 0.09 | Unknown | |
| | | | | | 0.95 | 0.14 | Unknown | |
| | | | | | 1.16 | 0.13 | 10-oxo DCT | |
| | | | | | 1.43 | 0.08 | 7-Epi-DCT | |
| | | | | | Total | 0.96 | | |
| | | 60 days | 41.4 | 97.0 | 0.22 | 0.17 | Unknown | Solution color changed from pale yellow to yellow |
| | | | | | 0.33 | 0.24 | Unknown | |
| | | | | | 0.36 | 0.09 | Unknown | |
| | | | | | 0.59 | 0.04 | Unknown | |
| | | | | | 0.84 | 0.15 | Unknown | |
| | | | | | 0.95 | 0.15 | Unknown | |
| | | | | | 1.16 | 0.12 | 10-oxo DCT | |
| | | | | | 1.44 | 0.08 | 7-Epi-DCT | |
| | | | | | Total | 1.04 | | |
| | | 90 days | 40.0 | 94.0 | 0.21 | 0.09 | Unknown | Solution color changed from yellow to a darker shade of yellow |
| | | | | | 0.33 | 0.14 | Unknown | |
| | | | | | 0.60 | 0.06 | Unknown | |
| | | | | | 0.84 | 0.51 | Unknown | |
| | | | | | 0.95 | 0.21 | Unknown | |
| | | | | | 1.17 | 0.20 | 10-oxo | |
| | | | | | 1.46 | 0.53 | 7-Epi-DCT | |
| | | | | | 1.60 | 0.10 | 7-epi-10-oxo | |
| | | | | | 2.25 | 0.14 | | |
| | | | | | Total | 1.98 | Unknown | |

TABLE EX-33D

Stability data for the following initial concentrate formulation, having lipoic acid (and/or dihydrolipoic acid and/or salts thereof) below the claim required amounts
Docetaxel 80 mg
Lipoic acid 0.5 mg
Glycofurol 1.0 Ml
Table EX-33D:

| Storage Temp. | Time period | % of Initial | RRT of Degradants | Degradant Area % | ID of Degradant |
|---|---|---|---|---|---|
| Initial | | 100 | 1.43 | 0.07 | Epi-DCT |
| 40° C. | 30 Days | 96 | 0.64 | 0.85 | Unknown |
| | | | 0.76 | 0.23 | Unknown |
| | | | 0.80 | 0.27 | Unknown |
| | | | 0.88 | 0.06 | Unknown |
| | | | 1.17 | 0.28 | 10-oxo-DCT |
| | | | 1.46 | 0.26 | Epi-DCT |
| | | | Total | 1.95 | |
| | 60 days | | Skipped due to technical reasons | | |
| | 90 Days | 89 | 0.24 | 0.06 | Unknown |
| | | | 0.47 | 0.13 | Unknown |
| | | | 0.63 | 2.89 | Unknown |
| | | | 0.70 | 0.05 | Unknown |
| | | | 0.75 | 1.48 | Unknown |
| | | | 0.78 | 0.56 | Unknown |
| | | | 0.89 | 0.18 | Unknown |
| | | | 1.17 | 0.46 | 10-oxo-DCT |
| | | | 1.46 | 0.35 | Epi-DCT |
| | | | Total | 6.16 | |
| 25° C. | 90 Days | 98 | 0.64 | 0.76 | Unknown |
| | | | 0.76 | 0.12 | Unknown |
| | | | 0.80 | 0.17 | Unknown |
| | | | 0.87 | 0.05 | Unknown |
| | | | 1.18 | 0.26 | 10-oxo-DCT |
| | | | 1.48 | 0.12 | Epi-DCT |

TABLE EX-33E

Stability data for the following initial concentrate formulation, having lipoic acid (and/or dihydrolipoic acid and/or salts thereof) below the claim required amounts,
Docetaxel 80 mg
Lipoic acid 1.0 mg
Glycofurol qs 1.0 mL

| Storage Temp. | Time period | % of Initial | RRT of Degradants | Degradant Area % | ID of Degradant |
|---|---|---|---|---|---|
| Initial | | 100 | 1.43 | 0.07 | Epi-DCT |
| 40° C. | 30 Days | 99 | 0.64 | 0.14 | Unknown |
| | | | 0.87 | 0.05 | Unknown |
| | | | 1.17 | 0.20 | 10-oxo-DCT |
| | | | 1.46 | 0.27 | Epi-DCT |
| | | | 1.62 | 0.05 | Unknown |
| | | | Total | 0.71 | |
| | 60 days | 97 | 0.64 | 1.66 | Unknown |
| | | | 0.75 | 0.44 | Unknown |
| | | | 0.79 | 0.19 | Unknown |
| | | | 1.17 | 0.30 | 10-oxo-DCT |
| | | | 1.46 | 0.20 | Epi-DCT |
| | | | Total | 2.80 | |
| | 90 Days | 91 | 0.19 | 0.25 | Unknown |
| | | | 0.23 | 0.05 | Unknown |
| | | | 0.63 | 3.73 | Unknown |
| | | | 0.75 | 2.44 | Unknown |
| | | | 0.78 | 0.84 | Unknown |
| | | | 0.89 | 0.33 | Unknown |
| | | | 1.18 | 0.48 | 10-oxo-DCT |
| | | | 1.47 | 0.29 | Epi-DCT |
| | | | Total | 8.41 | |

TABLE EX-33E-continued

Stability data for the following initial concentrate formulation, having lipoic acid (and/or dihydrolipoic acid and/or salts thereof) below the claim required amounts,
Docetaxel 80 mg
Lipoic acid 1.0 mg
Glycofurol qs 1.0 mL

| Storage Temp. | Time period | % of Initial | RRT of Degradants | Degradant Area % | ID of Degradant |
|---|---|---|---|---|---|
| 25° C. | 90 Days | 98 | 0.87 | 0.09 | Unknown |
| | | | 1.19 | 0.18 | 10-oxo-DCT |
| | | | 1.48 | 0.25 | Epi-DCT |
| | | | 1.66 | 0.07 | Unknown |
| | | | Total | 0.59 | |

TABLE EX-33F

Stability data for the following formulation having lipoic acid (and/or dihydrolipoic acid and/or salts thereof) below the claim required amounts
Docetaxel 80 mg
Lipoic acid 2.0 mg
Glycofurol qs 1.0 mL
TABLE EX-33F

| Storage Temp. | Time period | % of Initial | RRT of Degradants | Degradant Area % | ID of Degradant |
|---|---|---|---|---|---|
| Initial | | 100 | 1.43 | 0.07 | Epi-DCT |
| 40 C. | 30 Days | 99 | 0.87 | 0.06 | Unknown |
| | | | 1.17 | 0.17 | 10-oxo-DCT |
| | | | 1.46 | 0.22 | Epi-DCT |
| | | | Total | 0.45 | |
| | 60 Days | 97 | 0.63 | 1.07 | Unknown |
| | | | 0.75 | 0.19 | Unknown |
| | | | 0.79 | 0.06 | Unknown |
| | | | 1.17 | 0.25 | 10-oxo-DCT |
| | | | 1.47 | 0.20 | Epi-DCT |
| | | | Total | 1.76 | |
| | 90 Days | 93 | 0.19 | 0.14 | Unknown |
| | | | 0.28 | 0.05 | Unknown |
| | | | 0.63 | 2.76 | Unknown |
| | | | 0.75 | 1.10 | Unknown |
| | | | 0.78 | 0.39 | Unknown |
| | | | 0.88 | 0.11 | Unknown |
| | | | 1.18 | 0.35 | 10-oxo-DCT |
| | | | 1.47 | 0.42 | Epi-DCT |
| | | | 1.64 | 0.07 | Unknown |
| | | | Total | 5.39 | |
| 25 C. | 90 Days | 98 | 0.87 | 0.09 | Unknown |
| | | | 1.19 | 0.18 | 10-oxo-DCT |
| | | | 1.48 | 0.25 | Epi-DCT |
| | | | 1.66 | 0.07 | Unknown |
| | | | Total | 0.25 | |

TABLE EX-33G

Stability date for the following formulation, having lipoic acid (and/or dihydrolipoic acid and/or salts thereof) within the claim required amounts
DCT 80 mg/ml
Lipoic acid 5 mg/ml
Glycofurol qs to 1.0 ml

| Storage Temp. | Time period | Content mg/ml | % of Initial | RRT of Degradants | Degradant Area % | ID of Degradant |
|---|---|---|---|---|---|---|
| Initial | | 70.6 | 100 | 1.43 | 0.06 | 7-Epi-DCT |
| 40° C. | 30 Days | 70.0 | 99 | 0.87 | 0.06 | Unknown |
| | | | | 1.18 | 0.11 | 10-oxo-DCT |
| | | | | 1.46 | 0.21 | 7-Epi-DCT |
| | | | | Total | 0.38 | |
| | 60 Days | 69.9 | 99 | 0.85 | 0.10 | Unknown |
| | | | | 1.17 | 0.16 | 10-oxo-DCT |
| | | | | 1.46 | 0.34 | 7-Epi-DCT |
| | | | | 1.61 | 0.05 | Unknown |
| | | | | Total | 0.65 | |
| | 90 Days | 69.7 | 99 | 0.85 | 0.14 | Unknown |
| | | | | 1.18 | 0.29 | 10-oxo-DCT |
| | | | | 1.47 | 0.31 | 7-Epi-DCT |
| | | | | 1.64 | 0.09 | Unknown |
| | | | | Total | 0.83 | |
| 25° C. | 90 Days | 70.6 | 100 | 0.87 | 0.06 | Unknown |
| | | | | 1.19 | 0.10 | 10-oxo-DCT |
| | | | | 1.48 | 0.12 | 7-Epi-DCT |
| | | | | Total | 0.28 | |

Example 34

The concentrates (a) of Examples 1-24 are diluted with the diluents formulation of Examples 25-26 or (b) corresponding to Examples 1-24 except that they are devoid of α-lipoic acid, a salt thereof, dihydrolipoic acid, and a salt thereof are diluted with the diluents of Examples 27-32 to result in intermediate concentrates having docetaxel concentrations (based on the free docetaxel moiety) of 10 mg/ml and containing a member selected from α-lipoic acid, a salt thereof, dihydrolipoic acid, a salt thereof, and mixtures thereof. These intermediate concentrates are added to standard infusion fluids suitable for administration as an infusion of the docetaxel at an infusion administration concentration of 0.74 mg docetaxel moiety/ml of infusion solution. The diluted solution is clear for over a week.

I claim:

1. A solid docetaxel formulation comprising a first component comprising docetaxel or a pharmaceutically acceptable salt thereof and a second component comprising a member selected from the group consisting of α-lipoic acid or a pharmaceutically acceptable salt thereof, dihydrolipoic acid or a pharmaceutically acceptable salt thereof, and mixtures thereof, where the second component is present and in an amount of greater than 0.025 to less than 2.5 parts by weight based on α-lipoic acid or dihydrolipoic acid respectively per 1 part of said first component based on free docetaxel.

2. The formulation of claim 1 wherein said second component is present in an amount of more than 0.025 parts by weight to not more than 0.2 parts by weight based on said α-lipoic acid or dihydrolipoic acid respectively per 1 part by weight of said first component based on free docetaxel.

3. The formulation of claim 1 wherein said second component is present in an amount of more than 0.03125 parts by weight to not more than 0.1875 parts by weight based on said α-lipoic acid or dihydrolipoic acid respectively per 1 part by weight of said first component based on free docetaxel.

4. The formulation of claim 1 wherein said second component is present in an amount of more than 0.0375 parts by weight to not more than 0.1275 parts by weight based on said α-lipoic acid or dihydrolipoic acid respectively per 1 part by weight of said first component based on free docetaxel.

5. The formulation of claim 1 wherein said second component is present in an amount of more than 0.05 parts by weight to not more than 0.09375 parts by weight based on said α-lipoic acid or dihydrolipoic acid respectively per 1 part by weight of said first component based on free docetaxel.

6. The formulation of claim 1 wherein said second component is present in an amount of about 0.0625 parts by weight based on said α-lipoic acid or dihydrolipoic acid respectively per 1 part by weight of said first component based on free docetaxel.

7. The formulation of claim 1 wherein said member is α-lipoic acid or a pharmaceutically acceptable salt thereof.

8. The formulation of claim 7 wherein said member is selected from the group consisting of α-lipoic acid, the sodium salt thereof, and the potassium salt thereof, and mixtures thereof.

9. The formulation of claim 1 wherein said member is dihydrolipoic acid or a pharmaceutically acceptable salt thereof.

10. The formulation of claim 1 wherein said member is selected from the group consisting of dihydrolipoic acid, the sodium salt thereof, and the potassium salt thereof, and mixtures thereof.

11. A liquid solution docetaxel formulation comprising
a first component comprising docetaxel or a pharmaceutically acceptable salt thereof in an amount less than 15 mg (based on free docetaxel)/ml of said solution;
a second component comprising a member selected from the group consisting of α-lipoic acid or a pharmaceutically acceptable salt thereof, dihydrolipoic acid or a pharmaceutically acceptable salt thereof, and mixtures thereof, and in an amount of greater than 0.025 to less than 2.5 parts by weight based on α-lipoic acid or dihydrolipoic acid respectively per part of said first component based on free docetaxel; and
a solvent capable of dissolving said docetaxel at a concentration of at least up to 15 mg/ml of solution.

12. The formulation of claim 11 comprising

| | | |
|---|---|---|
| (a) | Docetaxel or salt thereof | 10-<15 mg |
| (b) | Glycofurol | 1 ml |
| (c) | dihydroLipoic acid or salt thereof | >0.025-<2.5 mg (based on dihydrolipoic acid moiety) per mg of docetaxel moiety |
| (d) | TPGS | 750-2000 mg |
| (e) | PEG-400 | 2.0-3.0 ml |
| (f) | NaCl | 0-100 mg |
| (g) | Water | qs to 8 ml. |

13. A liquid solution docetaxel formulation comprising
a first component comprising docetaxel or a pharmaceutically acceptable salt thereof in an amount in excess of 10 mg/ml of said solution;
a second component comprising a member selected from the group consisting of α-lipoic acid or a pharmaceutically acceptable salt thereof, dihydrolipoic acid or a pharmaceutically acceptable salt thereof, and mixtures thereof, and in an amount of greater than 0.025 to less than 2.5 parts by weight based on α-lipoic acid or dihydrolipoic acid respectively per part of said first component based on free docetaxel; and
a solvent for said docetaxel capable of dissolving said docetaxel in an amount in excess of 10 mg/ml of solution.

14. The formulation of claim 11 comprising

| | | |
|---|---|---|
| (a) | Docetaxel or salt there of | 10-<15 mg |
| (b) | Glycofurol | 1 ml |
| (c) | α-Lipoic acid or salt thereof | >0.025-<2.5 mg (based on lipoic acid moiety) per mg of docetaxel moiety |
| (d) | TPGS | 750-2000 mg |
| (e) | PEG-400 | 2.0-3.0 ml |
| (f) | NaCl | 0-100 mg |
| (g) | Water | qs to 8 ml. |

15. An infusion solution comprising
a first component comprising docetaxel or a pharmaceutically acceptable salt thereof in an infusion suitable concentration;
a second component comprising a member selected from the group consisting of α-lipoic acid or a pharmaceutically acceptable salt thereof, dihydrolipoic acid or a pharmaceutically acceptable salt thereof, and mixtures thereof,
a solvent for said first component; said solvent capable of dissolving said first component; and an infusion liquid diluent in an amount such that said first component is present in an infusion acceptable concentration and said second component is present in an amount of from more than 0.025 parts to less than 2.5 parts by weight of α-lipoic acid (or a pharmaceutically acceptable salt thereof based upon free α-lipoic acid) or dihydrolipoic acid (or a pharmaceutically acceptable salt thereof based upon free dihydrolipoic acid) per part by weight of said first component based on free docetaxel.

16. A method of preparing an infusion solution containing docetaxel or a pharmaceutically acceptable salt thereof, said infusion solution comprising
(a) docetaxel or a pharmaceutically acceptable salt thereof,
(b) a member selected from the group consisting of α-lipoic acid or a pharmaceutically acceptable salt thereof, dihydrolipoic acid or a pharmaceutically acceptable salt thereof, and mixtures thereof; and
(c) an infusion suitable infusion fluid;
comprising firstly combining said member with at least one of
(a) a solid formulation of docetaxel or pharmaceutically acceptable salt thereof;
(b) a liquid solution of docetaxel or a pharmaceutically acceptable salt thereof; to result in a combination product and
further secondly combining said combination product with said infusion fluid;
said firstly combining being in an amount for said first member to be present in at least said infusion solution in an amount of from more than 0.025 parts to less than 2.5 parts by weight based on free α-lipoic acid or free dihydrolipoic acid respectively per 1 part by weight of said docetaxel or pharmaceutically acceptable salt thereof based on free docetaxel.

17. A method of preparing a concentrate solution containing docetaxel or a pharmaceutically acceptable salt thereof, said concentrate solution comprising
(a) docetaxel or a pharmaceutically acceptable salt thereof,
(b) a member selected from the group consisting of α-lipoic acid or a pharmaceutically acceptable salt thereof, dihydrolipoic acid or a pharmaceutically acceptable salt thereof, and mixtures thereof, and
(c) a solvent for said docetaxel or pharmaceutically acceptable salt thereof comprising combining said member with at least one of
(a) a solid formulation of docetaxel or pharmaceutically acceptable salt thereof; and
(b) a liquid solution of docetaxel or a pharmaceutically acceptable salt thereof;
in an amount for said member to be present in at least said concentrate solution in an amount of from more than 0.025 parts to less than 2.5 parts by weight based on free α-lipoic acid or free dihydrolipoic acid respectively per 1 part by weight of said docetaxel or pharmaceutically acceptable salt thereof based on free docetaxel.

18. A method of treating a docetaxel responsive condition in a patient in need thereof via an infusion comprising administering to said patient a pharmaceutically effective amount for said docetaxel responsive condition of an infusion containing docetaxel or a pharmaceutically acceptable salt thereof and a member selected from the group consisting of α-lipoic acid or a pharmaceutically acceptable salt thereof, dihydrolipoic acid or a pharmaceutically acceptable salt thereof, and mixtures thereof, in an amount of from more than 0.025 parts to less than 2.5 parts by weight based on free α-lipoic acid or free dihydrolipoic acid respectively per 1 part by weight of said docetaxel or pharmaceutically acceptable salt thereof based on free docetaxel.

19. A method of extending the stability of a liquid concentrate formulation containing docetaxel or a pharmaceutically acceptable salt thereof comprising incorporating into said concentrate formulation a member selected from the group consisting of α-lipoic acid or a pharmaceutically acceptable salt thereof, dihydrolipoic acid or a pharmaceutically acceptable salt thereof, and mixtures thereof, in an amount of from more than 0.025 parts to less than 2.5 parts by weight based on free α-lipoic acid or free dihydrolipoic acid respectively per 1 part by weight of said docetaxel or pharmaceutically acceptable salt thereof based on free docetaxel.

20. A method of extending the time period in which a docetaxel liquid formulation is to be used, measured between
   (a) dilution of a more highly concentrated formulation to concentrations of less than 15 mg docetaxel/ml of solution until
   (b) completion of administration of an infusion made therefrom; said extending being measured between (a) a period of not more than 4 hours to (b) a period greater than 4 hours;
   comprising including a member selected from the group consisting of α-lipoic acid or a pharmaceutically acceptable salt thereof, dihydrolipoic acid or a pharmaceutically acceptable salt thereof, and mixtures thereof, in an amount of from more than 0.025 parts to less than 2.5 parts by weight based on free α-lipoic acid or free dihydrolipoic acid respectively per 1 part by weight of said docetaxel or pharmaceutically acceptable salt thereof based on free docetaxel into said formulation and inclusion of said member is at least one of (a) a point in time when said more highly concentrated formulation is diluted to concentrations of less than about 15 mg/ml of docetaxel or pharmaceutically acceptable salt thereof based on free docetaxel, or (b) inclusion in said more highly concentrated formulation prior to said dilution, or (c) inclusion as a blend with said solid docetaxel or pharmaceutically acceptable salt thereof.

\* \* \* \* \*